United States Patent [19]

Buu-Hoi et al.

[11] 3,954,871
[45] May 4, 1976

[54] 1-(4-ALKYLTHIOPHENY)-2-SUBSTITUTED AMINO-ALCOHOLS AND THEIR SALTS

[75] Inventors: Nguyen Phuc Buu-Hoi, Hue, South Vietnam; Georges E. Lambelin, Brussels, Belgium; Joseph L. Roba, Wanlin, Belgium; Claude Gillet; Guy D. Jacques, both of Brussels, Belgium

[73] Assignee: Continental Pharma, Ixelles, Belgium

[22] Filed: Mar. 29, 1974

[21] Appl. No.: 456,216

Related U.S. Application Data

[63] Continuation of Ser. No. 74,117, Sept. 21, 1970, abandoned.

[30] Foreign Application Priority Data

Oct. 1, 1969  Belgium .............................. 739678
Sept. 3, 1970  Belgium .............................. 93537

[52] U.S. Cl. ........................ 260/570.6; 260/239 B;
260/247.1 R; 260/268 R; 260/293.73;
260/307 A; 260/309; 260/348 R; 260/455 R;
260/456 A; 260/470; 260/501.19; 260/516;
260/570.5 C; 260/570.5 P; 260/573;
424/248; 424/250; 424/267; 424/273;
424/316; 424/330
[51] Int. Cl.² .......................................... C07C 91/22
[58] Field of Search ................. 260/501.17, 501.19, 260/570.6

[56] References Cited
OTHER PUBLICATIONS
Buu–Hoi et al., "Chemical Abstracts," Vol. 73, p. 344, Section No. 109490t, (1970).

*Primary Examiner*—Robert V. Hines
*Attorney, Agent, or Firm*—Stevens, Davis, Miller & Mosher

[57] ABSTRACT

The new amino-alcohols according to the invention are represented by the formula

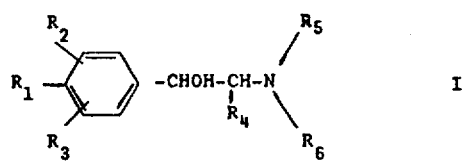

wherein: $R_1$ represents a RS, RSO or $RSO_2$ group in which R is a linear or branched alkyl group ($C_1$–$C_{10}$), an acetyl radical or hydrogen; $R_2$ and $R_3$, which may be identical or different, represent a halogen atom or an alkyl ($C_1$–$C_3$), amino, alkylamino ($C_1$–$C_4$), acylamino, nitro, carboxy, carbalkoxy, trifluoromethyl, alkoxy ($C_1$–$C_4$) or alkylthio ($C_1$–$C_4$) radical; $R_4$ represents hydrogen or a linear or branched alkyl radical containing 1 – 4 carbon atoms; $R_5$ and $R_6$, which may be identical or different, represent hydrogen, a substituted or not, linear or branched alkyl ($C_1$–$C_{16}$) radical, a cycloalkyl ($C_5$–$C_6$) radical, an alkynyl ($C_3$–$C_4$) radical, an alkenyl ($C_3$–$C_4$) radical or a heterocycle of the kind piperidine, morpholine, pyridine or pyridimine, $R_5$ and $R_6$ can also form with adjacent nitrogen atom a heterocyclic radical, substituted or not; one of said $R_2$ and $R_3$ can be a hydrogen atom or can be both a hydrogen atom provided that simultaneously R is a lower alkyl ($C_1$–$C_3$) radical in the group RS, $R_4$ and $R_5$ are hydrogen atoms and $R_6$ is an isopropyl or t-butyl radical or if simultaneously R is a methyl radical in the group $RSO_2$, $R_4$ and $R_5$ are hydrogen atoms and $R_6$ is an isopropyl radical.

When $R_5$ and $R_6$ represent an alkyl, the latter can be substituted by amino, alkylamino, hydroxy, alkoxy, phenoxy, substituted phenoxy, phenyl, substituted phenyl radical or a heterocycle such as piperidino or morpholino.

9 Claims, No Drawings

1-(4-ALKYLTHIOPHENY)-2-SUBSTITUTED AMINO-ALCOHOLS AND THEIR SALTS

This is a continuation of application Ser. No. 74,117, filed Sept. 21, 1970, and now abandoned.

This invention relates to new amino-alcohols, salts thereof, preparation of said new compounds, as well as to their use in therapeutical field.

The new amino-alcohols according to the invention are represented by the formula

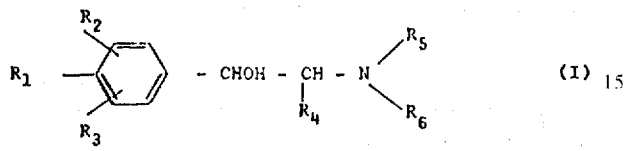

wherein: $R_1$ represents a RS, RSO or $RSO_2$ group in which R is a linear or branched alkyl group $(C_1-C_{10})$, an acetyl radical or hydrogen; $R_2$ and $R_3$, which may be identical or different, represent a halogen atom or an alkyl $(C_1-C_3)$, amino, alkylamino $(C_1-C_4)$, acylamino, nitro, carboxy, carbalkoxy, trifluoromethyl, alkoxy $(C_1-C_4)$ or alkylthio $(C_1-C_4)$ radical; $R_4$ represents hydrogen or a linear or branched alkyl radical containing 1-4 carbon atoms; $R_5$ and $R_6$, which may be identical or different, represent hydrogen, a substituted or not, linear or branched alkyl $(C_1-C_{16})$ radical, a cycloalkyl $(C_5-C_6)$ radical, an alkynyl $(C_3-C_4)$ radical, an alkenyl $(C_3-C_4)$ radical or a heterocycle of the kind piperidine, morpholine, pyridine or pyridimine, $R_5$ and $R_6$ can also form with adjacent nitrogen atom a heterocyclic radical, substituted or not; one of said $R_2$ and $R_3$ can be a hydrogen atom or can be both a hydrogen atom provided that simultaneously R is a lower alkyl $(C_1-C_3)$ radical in the group RS, $R_4$ and $R_5$ are hydrogen atoms and $R_6$ is an isopropyl or t-butyl radical or if simultaneously R is a methyl radical in the group $RSO_2$, $R_4$ and $R_5$ are hydrogen atoms and $R_6$ is an isopropyl radical.

When $R_5$ and $R_6$ represent an alkyl, the latter can be substituted by amino, alkylamino, hydroxy, alkoxy, phenoxy, substituted phenoxy, phenyl, substituted phenyl radical or a heterocycle such as piperidino or morpholino.

SPECIFIC EXAMPLES OF THE INVENTION

Examples of amino-alcohols having preceding formula I are:

1-(3-methyl-4-methylthiophenyl)-2-isopropylaminoethanol
1-(3-methyl-4-methylthiophenyl-2-cyclopentylaminoethanol
1-(3-ethyl-4-methylthiophenyl)-2-isopropylaminoethanol
1-(3-ethyl-4-methylthiophenyl)-2-secbutylaminoethanol
1-(2-chloro-4-methylthiophenyl)-2-terbutylaminoethanol
1-(3-chloro-5-methyl-4-methylthiophenyl-2-isopropylaminoethanol
1-(4-isobutylthio-3-methylphenyl)-2-piperidinoethanol
1-(4-n-butylthio-3-methylphenyl)-2-(3-methoxypropylamino)ethanol
1-(3-methyl-4-n-octylthiophenyl)-2-piperidinoethanol
1-(3-methyl-4-methylthiophenyl)-2-n-octylaminoethanol
1-(4-isopropylthio-3-methylphenyl)-2-n-octylaminoethanol
1-3-methyl-4-methylthiophenyl)-2-(α-methyl-3,4-dichlorophenyle-thylamino)ethanol
1-(2-methyl-4-methylthiophenyl)-2-n-octylaminoethanol
1-(4-n-hexylthio-3-methylphenyl)-2-n-butylaminoethanol
1-(3-methyl-4-methylsulphonylphenyl)-2-isopropylaminoethanol
1-(3-methyl-4-methylthiophenyl)-2-[4-(p-chlorophenyl)piperazino]ethanol
1-(3-methyl-4-methylsulfonylphenyl)-2-terbutylaminoethanol
1-(3-methoxy-4-methylthiophenyl)-2-piperidinoethanol
1-(3-methyl-4-methylthiophenyl)-2(4-hydroxypiperidino)ethanol
1-(3-chloro-4-methylthiophenyl)-2-(N,N-diethylaminoethylamino) ethanol
1-(4-methylthiophenyl)-2-n-octylaminoethanol
1-(4-n-butylthio-3-methylphenyl)-2-dicyclohexylaminoethanol
1-(3-chloro-4-methylthiophenyl)-2-(3-hydroxypropylamino)ethanol
1-(4-n-butylthio-3-methylphenyl)-2-allylaminoethanol
1-(3-chloro-4-methylphenyl)-2-N-(1-phenyl-2-aminopropanol)ethanol
1-(3-chloro-4-methylthiophenyl)-2-(3-N-morpholinopropylamino) ethanol
1-(3-chloro-4-methylthiophenyl)-2-(1-methyl-2-phenoxyethylamino) ethanol
1-(3-methyl-4-methylthiophenyl)-2-N-imidazolylethanol
1-(3-methyl-4-methylthiophenyl)-2-N-(4-benzylpiperidino)ethanol
1-(4-methylthio-3-nitrophenyl)-2-isopropylaminoethanol
1-(3,4-dimethylthiophenyl)-2-terbutylaminoethanol
1-(3-fluoro-4-methylthiophenyl)-2-isopropylaminoethanol
1-(4-methylthio-3-trifluoromethylphenyl)-2-isopropylaminoethanol
1-(4-acetylthio-3-methylphenyl)-2-terbutylaminoethanol
1-(3-carboxy-4-methylthiophenyl)-2-piperidinoethanol
1-(3-methyl-4-methylsulfinyl)-2-isopropylaminoethanol
1-(3-chloro-4-methylthiophenyl)-2-secbutylaminoethanol
1-(2-chloro-4-methylthiophenyl)-2-secbutylaminoethanol
1-(4-isopropylthio-3-methylphenyl)-2-n-butylaminoethanol
1-(4-n-butylthio-3-methylphenyl)-2-(4-methylpiperidino)ethanol
1-(4-isopropylthio-3-methylphenyl)-2-t-butylaminoethanol
1-(4-n-amylthio-3-methylphenyl-2-n-butylaminoethanol
1-(4-isopropylthio-3-methylphenyl)-2-cyclohexylaminoethanol This invention also includes preparation of non toxical salts of amino-alcohols of formula I, such as hydrochlorides, hydrobromides, phosphates, sulfates, oxalates, lactates, tartarates, acetates, citrates, maleates and the like.

The compounds according to the invention comprise one or more asymmetric carbon atoms and can thus exist as optically active isomers, racemics and diastereoisomers. All said different forms are included in the present invention.

Thus if in the general formula I, $R_4$, $R_5$ and $R_6$ comprise no asymmetry centre, one obtains a racemic mixture of enantiomers, said mixture can be resolved by means of well known processes such as for example formation of a salt with an optically active acid and separation of the mixture of diastereoisomer salts through fractional crystallisation, chromatography, distillation. As resolution agent, one uses for example the optically active forms of tartaric, diacetyltartaric, dibenzoyltartaric, ditoluyltartaric, camphorsulfonic, bromocamphorsulfonic, malic and mandelic acids. If in formula I, one or more of $R_4$, $R_5$ and $R_6$ contain an asymmetry element, two or more diastereoisomer mixtures are obtained. Said diastereoisomer mixtures can very easily be separated through fractional crystallisation for example and the racemics can be resolved through already previously cited conventional processes.

It is known that the 1-aryl-2-aminoethanol derivatives have the property to block the $\beta$-adrenergic receptors.

It has been found that if the compounds of general formula I always have said property, while being free of sympathicomimetic effects, they are moreover provided with other pharmacological activities which differentiate them from known products.

Thus the products of the invention have a marked peripherical vasodilatator activity which appears at very low doses.

It has also been remarked that said products can induce an oxygen saving at the level of the myocardium.

Due to the fact that the blocking agents of the adrenergic receptors are often administrated in case of deficiency of heart oxygenation (pectoris angina), the association of an activity allowing an increase of the energetic efficiency of the heart with said $\beta$-lytic action is of an obvious therapeutical interest.

The products according to the invention are also endowed with an anti-arrhythmic and hypotensive activity. The pharmacological characteristics of said products must allow use thereof in the treatment and prophylaxis of affections of coronary vessels, in the treatment of cardiac arrhythmiae, as peripheral vasodilatator and as anti-hyportensor.

Their blocking activity of $\beta$-adrenergic receptors allows an action on metabolic effects of adrenergic amines and more particularly the mobilization of glucose and free fatty acids. Moreover, said compounds show a low toxicity, which allows a long-lasting therapy securely.

This invention also claims pharmaceutical compositions containing, as active ingredient, at least one compound of general formula I and/or a salt thereof with a pharmaceutical excipient. Said compositions are presented so as to be able to be administrated orally, rectally or parenterally.

Thus for example the compositions for oral administration can be liquid or solid and presented as tablets, capsules, granules, powders, syrups or suspensions; such compositions comprise additives and excipients, generally used in galenic pharmacy, inert diluents, desintegration agents, binding agents and lubricating agents, such as lactose, starch, talc, gelatin, stearic acid, silicic acid, magnesium stearate, polyvinylpyrrolidone, calcium phosphate, calcium carbonate and the like.

Such preparations can be made so as to increase the desintegration time and consequently the duration of action of the active principle.

The aqueous suspensions, oily emulsions and solutions are prepared in the presence of sweetening agents, such as dextrose or glycerol, of perfuming agents, such as vanilline for example, and can also contain thickening agents, wetting agents, preservative agents.

The oily emulsions and solutions are prepared in an oil of vegetal or animal origin and can contain emulsifying, perfuming, dispersing, sweetening and anti-oxidizing agents. For parenteral administration, one uses as vehicle sterile water, an aqueous solution of polyvinylpyrrolidone, peanut oil, ethyl oleate and the like. Said injectable aqueous or oily solutions can contain thickening, wetting, dispersing and gelifying agents.

The new compounds according to the invention are prepared according to the general process forming the subject of the present invention and defined as follows:

New amino-alcohols and salts thereof are prepared from a compound having the formula:

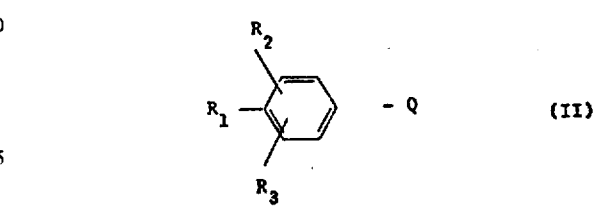

or eventually, according the the value of Q, from a salt of a compound having said formula, wherein $R_1$, $R_2$ and $R_3$ have the meaning given hereinbefore and Q represents one of the following groups.

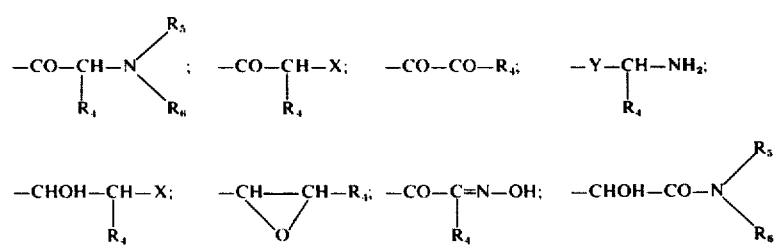

In said groups, $R_4$, $R_5$ and $R_6$ have also the meaning hereinbefore given while Y represents a —CO— or —CHOH— radical and X represents a halogen atom.

This general process can be carried out according to several ways which are substantially determined by the starting product, i.e. by the value of Q in formula II.

Said various modes of preparation are described hereinafter and for easiness are successively defined as processes A to E.

Process A

According to this way to proceed, an α-aminoketone having formula (II), wherein Q represents the group

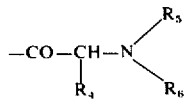

in which $R_1$ to $R_6$ have the meaning given hereinabove is reduced.

This reduction can be made in the usual way, for example by hydrogenation in presence of a catalyst, such as palladium on carbon, nickel Raney or platinum, in the presence of a solvent such as methanol or ethanol, at ordinary or high pressure, or still by action of alkali metal hydrides such as sodium borohydride, in a solvent such as methanol or ethanol, preferably at low temperature, or by action of aluminium and lithium hydride in ether or tetrahydrofuran, preferably at low temperature, or still by action of aluminum alkoxyde, such as aluminium isopropoxide, in a solvent such as isopropanol, the most avantageously at reflux of the latter. It is to be noted that the reduction can eventually be made on a salt of compound II (hydrochloride, oxalate and the like) in case of the preparation of an amino-alcohol salt.

The starting compounds of general formula II, wherein Q has the above meaning are easily obtainable, for example by action of an amine $R_5R_6NH$ on a α-halogenoketone in inert solvents, such as ether, benzene, chloroform, dioxan, a lower alcohol such as methanol, ethanol or isopropanol, or also acetonitrile, this in the easiest way at ordinary temperature or in the cold. Said starting compounds can also be obtained by Houben-Hoesch reaction from an aminoalkylnitrile of the type CN-CH(R₄)—

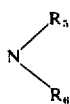

and from suitably substituted benzene compounds. H.D. Moed Rec. Trav. chim. 71, 933 (1952).

Process B

According to this other mode of preparation, a compound of formula (II) wherein Q represents one of the groups

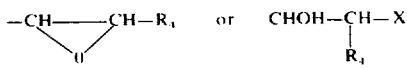

is reacted with an amine of the type $R_5R_6NH$, formulae in which $R_1$ to $R_6$ have the meaning given previously and X represents a halogen atom.

This particular mode of preparation can be more completely represented by the following scheme:

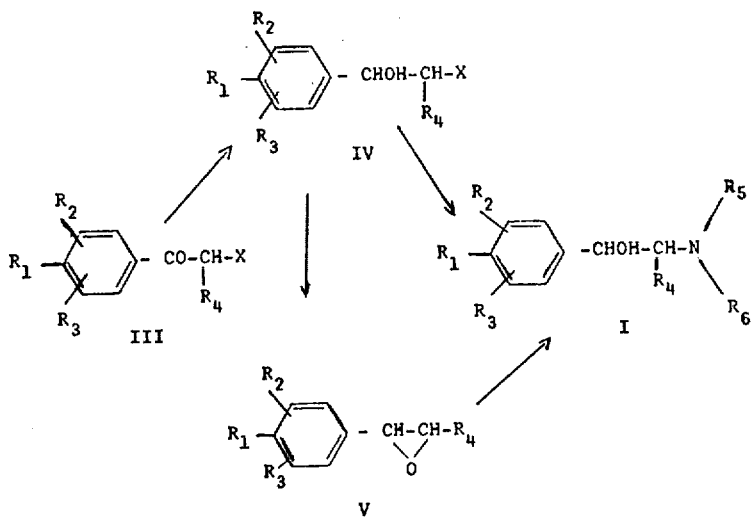

The reduction of compounds III is made according to conventional processes already described previously; it is known in the literature that one can obtain either compound IV or a mixture of compounds IV and V, and this more particularly when reductions are made by metal hydrides. Each of both said compounds or the mixture can be directly reacted with an amine derivative $R_5R_6NH$. It is also well known in the literature that the action of an amine on a compound of type IV so as to obtain compound I passes through an intermediate epoxide of type V; for practical reasons, it is however sometimes easier to quantitatively form epoxide V by treating product IV with a basic agent such as sodium hydroxide, potassium hydroxide or a sodium alkoxide.

The opening of the epoxide by amine $R_5R_6NH$ is made in a solvent such as methanol, ethanol, isopropanol, dioxan, benzene, dimethylformamide, or also without solvent in the presence of an excess of the amine derivative, at a temperature between room temperature and reflux temperature of the selected solvent. The reaction can also avantageously be made under pressure in an autoclave and a condensation agent, such as sodium hydroxide or acetate can be used.

Compounds I can also be obtained by starting from compound IV by action of an amine $R_5R_6NH$ in a solvent, such as dioxan, chloroform, ethanol, isopropanol or diglyme, this the most easily at reflux temperature of the selected solvent; this reaction can be carried out in the presence of a product fixing liberated hydrogen halide, for example a mineral base or an excess of the amine used.

Starting products III are the most easily obtained by halogenation of the corresponding ketone, or also by Friedel-Crafts reaction by starting from suitably substituted benzene compound and from acid halide of the type X—CH(R₄)—COX (X = halogen).

An epoxide of type V can be obtained from suitably substituted benzaldehyde by action of dimethylsulfoxonium or dimethylsulfonium methylide. E.J. Corey J. Am. Chem. Soc. 87, 1353 (1956 A.Z. Britten Chem. & Ind. 771 (1968).

Process C

According to this way to proceed, new aminoalcohols of the invention are prepared by transforming a dicarbonyl compound of formula II, wherein Q represents the group

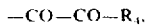

R₄ having the meaning given previously, by simultaneous action of an amine R₅R₆NH or of an hydroxylamine R₅R₆NOH and of a reducing agent, R₁ to R₅ having the meaning given previously, while R₆ represents hydrogen.

The reduction is carried out by catalytic hydrogenation in the presence of platinum or nickel Raney for example and in a solvent, such as methanol or ethanol either at atmospheric pressure or at a higher pressure. Reduction can also be made with an alkali metal hydride, for example sodium borohydride, in a solvent such as methanol, preferably at low temperature.

It is to be noted that reduction can be carried out on bisulfitic derivatives, hydrates or acetals deriving from precited dicarbonyl compound. Said compound is obtained the most easily when R₄ = H, from corresponding acetophenone by action of an oxidation agent, such as selenium dioxide, in a solvent, such as dioxan or water, by action of dimethyl sulfoxide on a α-halogenoacetophenone of the type responding to formula III [N. Kornblum J. Am. Chem. Soc. 79, 6562 (1957) ], also from α-dihalogenoacetophenones [F. Venien C.R. Acad. Sci. 266 1650 (1968) ] or still by means of conventional methods well known in the literature [Org. Synth. II 511 et 48 109 ].

Process D

According to this other mode of preparation, new amino-alcohols of the invention are obtained by reacting a starting compound of formula III, wherein Q represents the group

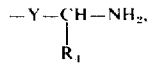

Y representing either radical —CO— or radical —CHOH— and R₄ having the previously mentioned meaning, under reducing conditions, with a carbonyl compound of the kind R₅R₆C = O, wherein R₅ represents hydrogen, linear or branched alkyl radical, alkenyl, alkenyl, alkynyl or substituted alkyl radical, and R₆ is a linear or branched alkyl radical or a substituted alkyl radical; R₅ and R₆ can form with ketone function an alicyclic or heterocyclic system; the alkyl radicals substituted in R₅ and R₆ are substituted by amino, alkylamino, hydroxy, phenoxy, substituted phenoxy, phenyl, substituted phenyl and heterocyclic groups.

The reducing alkylation of a starting compound of said type is carried out in the presence of hydrogen and of a hydrogenation catalyst, such as platinum oxide or palladium on carbon in a solvent, such as methanol, ethanol, ethyl acetate or glacial acetic acid, at ordinary pressure and more advantageously at higher pressure, or still with an alkali metal hydride such as sodium borohydride in a solvent, such as methanol, or aluminium and lithium hydride in a solvent, such as ether or tetrahydrofuran; when compound R₅R₆C = O is a ketone, one can work without solvent in the presence of an excess of ketone compound.

Said starting compound can be formed in situ from compounds of following types VI and VII:

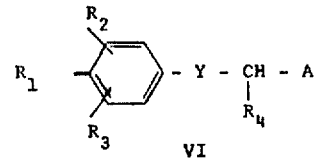

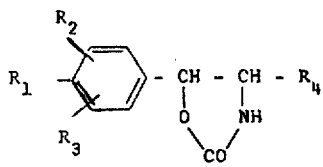

Y = CO, A = CN, —N₃, = N₂, = NOH, Y = CHOH, A = NO₂, —CN, —N₃

The α-cyanophenylketones (VI: Y = CO, A = CN) are obtained for example by reaction of suitably substituted benzoyl chloride with a cuprous cyanide [G. Zolss Sci. Pharm. 32 76 (1964) ], the α-azido and α-diazo alkylketones (VI: Y = CO, A = N₃ and = N₂) are prepared by processes well known in the literature (Houben-Weyl; Methoden der Organischen Chemie "Stickstoff Verbindingen I Vol 10/3); the insonitriketones (VI: Y = CO, A = NOH) are for example obtained from suitably substituted acetophenones (R₄ = H), propiophenones (R₄ = CH₃) and the like, by action of an alkyl nitrite, such as methyl, butyl or amyl nitrite in acid or basic medium; the 1-phenyl-2-nitroalkanols (VI: Y = CHH, A = — NO₂ ) are for example obtained by reaction of a suitably substituted benzaldehyde with a nitroalkane (nitromethane, nitroethane); the cyanohydrins (VI; Y = CHCH; A = CN) are obtained from a suitably substituted benzaldehyde and from hydrocyanic acid or a salt thereof with an alkali metal; the 1-phenyl-2-azidoalkanols (VI: Y = CHOH; A = N₃) are for example obtained by reaction of an epoxide of type V with sodium azide [C.A. Vanderwerf J. Am. Chem. Soc. 76 1231 (1954)]; an oxazolidone of type VII is for example obtained from a compound of the type

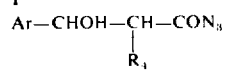

by Curtius rearrangement.

The above starting compound can also be obtained from a halogenoketone of type III by action of phthalimide, hexamethylene tetramine or ammoniac, or also from an epoxide of type N by action of ammoniac.

A halide of type R'X can also be used, wherein X represents a halogen and R' represents an alkyl, substituted alkyl, cycloalkyl, alkenyl or alkynyl radical.

Process E

According to this still other embodiment, aminoalcohols of the invention are obtained by reducing a starting compound of formula (II) wherein Q represents the —CHOH—CO—

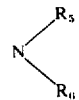

group, $R_5$ and $R_6$ having the meanings given previously.

The reduction of such a starting compound is the most easily carried out by means of an alkali metal hydride, such as lithium aluminium hydride, in a solvent such as diethyl ether or tetrahydrofuran at the cold or more avantageously at the reflux of the selected solvent.

Salts of amino-alcohols can be prepared, according to the invention, as previously mentioned, by the general process hereinbefore described.

Said process includes several variants. Generally, said salts can be prepared by well known methods of said general process, such as for example reaction in equimolecular amount of the amino-alcohol with an acid in a suitable solvent, such as an alcohol for example, then precipitation of the salt by addition of another solvent miscible with the first one acid, in which the salt is insoluble, such as ether for example; or still by neutralisation of an ethereal solution of the acid or base by the base or acid. The acids are either inorganic acids or organic acids. As inorganic acids, preferably hydrochloric, hydrobromic, sulfuric, phosphoric, perchloric acids and the like are used. The organic acids are either carboxylic acids, or sulfonic acids, such as formic, acetic, propionic, glycollic, lactic, citric, ascorbic, fumaric, maleic, pamoic, succinic, tartaric, phenylacetic, benzoic, p-aminobenzoic, anthranilic, p-hydroxybenzoic, salicylic, methanesulfonic, ethanedisulfonic acids and the like.

Another variant of the general process for preparing salts, in the case of Q in formula (II) represents one of the

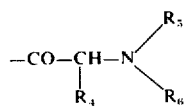

or

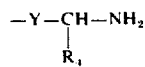

groups, Y and $R_4$ to $R_6$ having the meanings given previously, consists of directly making the reduction on a salt of this starting compound, so as to obtain a corresponding salt of an amino-alcohol having formula (I)

Said various variants of the process according to the invention are each hereinafter illustrated by means of relatively detailed preparation examples of a series of compounds said examples being then followed by a Table comprising characteristics of an important group of compounds which are prepared according to said various modes of preparation.

Compounds which, in this Table, do not present an asterisk (*) near their crude forumal were prepared according to at least one of the five variants of the process according to the invention, while compounds presenting an asterisk (*) were only prepared according to at least one of the variants defined hereinbefore as process A, B, E.

I. EXAMPLES OF PREPARATION ACCORDING TO PROCESS A

Example 1

1-(3-Methyl-4-methylthiophenyl)-2-t-butylaminobutanol a. To 160 g of aluminium chloride in 650 ml of chloroform, 125 g of butyryl chloride are added, then slowly 138 g of 1-methyl-2-methylthiobenzene are added at a temperature of 0°–5°C. The mixture is stirred for 2 hours at room temperature, then it is poured on ice and hydrochloric acid. The mixture is extracted with ether, dried on $MgSO_4$ and after evaporation of the solvent, the residue is distilled under vacuum. 166g of 3-methyl-4-methylthiobutyrophenone are obtained: Boiling point (B.P) = 132°–137°C (0.1 mm); Melting point (M.P.): 45°–46°C; Yield: 80%.

b. To 165 g of 3-methyl-4-methylthiobutyrophenone in 500 ml of anhydrous ether, 128 g of bromine are slowly added while stirring, the temperature being maintained at 10°C. After addition, the mixture is allowed to come back to room temperature and is treated with a 10% aqueous $NaHCO_3$ solution until discolouration of the organic phase. The latter is dried on $MgSO_4$ and the solvent is evaporated under vacuum. One obtains 160 g of 3-methyl-4-methylthio- α-bromobutyrophenone. MP (°C): 86.5 –88.5; Yield: 71%.

c. To 8.64 g of 3-methyl-4-methylthio-α-bromobutyrophenone in 100 ml of anhydrous acetonitrile, 8.76 g of t-butylamine are added and the mixture stirred for 24 hours at room temperature. Then 200 ml of ether are added and t-butylamine hydrobromide is filtered and washed with ether.

The organic phase is washed with water, dried on $MgSO_4$, then evaporated under vacuum. The residual red oil, the homogeneity of which is tested by thin layer chromatography is used as such in the following operation.

d. To the product obtained from the preceding operation and 100 ml of methanol, 2.3 g of sodium borohydride are slowly added with stirring and the temperature is maintained at 10°C. Stirring is still continued for 2 hours at room temperature, then the solvent is evaporated under vacuum. The residue is taken up with water and extracted with ether. The organic phase is dried on $MgSO_4$ and the hydrochloride is obtained by passing a stream of dry gaseous HCl.4.9 g of product are obtained. Total Yield of steps c and d: 51%. An analytical sample is several times recrystallised from a methanol-ether mixture. MP (°C): 235°–237°.

Centesimal analysis

Calc. (%): C: 60.45 H: 8.88 N: 4.41 Found (%): C: 60.25 H: 8.80 N-4.21

Example 2

1-(3-Methyl-4-methylthiophenyl)-2-N-(4-benzyl-piperidino)ethanol a. To 116 g of aluminium chloride in 600 ml of chloroform, 65 g of acetyl chloride are added, then slowly at a temperature of 0°–5°C, 105 g of 1-methyl-2-methylthiobenzene are added. The mixture is stirred for 2.5 hours at room temperature, then it is poured on ice and hydrochloric acid. It is extracted with ether, dried on $MgSO_4$ and after evaporation of the solvent, the residue is distilled out under vacuum. 109 g of 3-methyl-4-methylthioacetophenone are obtained. BP: 125° (1 mm); $n_D^{25}$ (refraction index) = 1.6120; Yield: 80%.

b. 600 g of 3-methyl-4-methylthioacetophenone (3.3 M) in 2000 ml of anydrous ether are dropwise treated with 169 ml of bromine (3.3 M). After addition, stirring is continued for 1.5 hour at room temperature, then one treats with 500 ml of a 10% bicarbonate solution. The organic phase is separated, dried on $MgSO_4$ and evaporated to the third of its initial volume. 300 ml of petroleum ether are added and the precipitate obtained is filtered. 790 g of 3-methyl-4-methylthio-α-bromoacetophenone are obtained. MP (°C): 66°–68°; Yield: 92%.

c. To 13.5 g of 3-methyl-4-methylthio-α-bromoacetophenone (0.05 M) in 100 ml of anhydrous ether, 17.5 g of 4-benzylpiperidine (0.1 M) are added and stirring is made overnight at room temperature. The hydrobromide is filtered from starting amine and solvent is evaporated under vacuum. The product obtained is directed used in the following operation.

d. To 16 g of 3-methyl-4-methylthio-α-N-(4-benzylpiperidino)acetophenone in 75 ml of methanol and 6 ml of 0.02 N sodium hydroxide, 1.5 g of sodium borohydride are slowly added with cooling in an ice bath. The mixture is stirred for 90 minutes at room temperature, then acidified with 2N HCl and diluted with an equal volume of water, then the aqueous phase is washed with ether. One basifies with 20% NaOH and extracts with ether. The organic phase is dried on magnesium sulfate and the hydrochloride is obtained by passing a stream of dry gaseous HCl. 14 g of product are obtained (Yield: 87%). A sample is recrystallised for analysis from a methanol-ether mixture. MP (°C): 234°–235°.

Centesimal analysis

% Calc.: C; 67.40 H: 7.71 N: 3.57 % Found: C: 67.47 H: 7.55 N: 3.55

Example 3

1-(3-Carbomethoxy-4-methylthiophenyl)-2-N-piperidionoethanol a. 3-Carbomethoxy-4-methylthioacetophenone The product is obtained by Friedal-Crafts reaction from 1-carbomethoxy-2-methylthiobenzene (CH$_3$COCl, CS$_2$, AlCl$_3$; reflux for 4 hours in waterbath). Yield: 43% (°C): 99°–102° isopropanol b. 3-Carbomethoxy-4-methylthio-α-bromoacetophenone Obtained by bromination of the preceding product with bromine (solvent: ether-dioxan 2/1, room temperature). Yield: 73 %; MP (°C): 145°–146°(benzene-ethyl acetate).

Centesimal analysis

% Calc.: C: 43.58 H: 3.66 % Found: C: 43.71 H: 3.85 c. 3-Carbomethoxy-4-methylthio-α-N-piperidinoacetophenone

Obtained by action of piperidine on the proceding product (solvent: acetonitrile, 24 hours at room temperature). The product is not purified; its homogeneity is tested by thin layer chromatography.

d. 1-(3-Carbomethoxy-4-methylthiophenyl)-2N-piperidinoethanol

Obtained by reduction with sodium borohydride of the preceding product (solvent: methanol, temperature: 10°C). Yield: 63 % MP (°C): 199°–201.5° (methanol-ether). Preparation of the corresponding hydrochloride as in the preceding examples.

Centesimal analysis

% Calc.: C: 55.56 H: 6.99 N: 4.05 % Found: C: 55.40 H: 6.90 N: 3.90

Example 4

1-(4-n-Butylthio-3-methylphenyl)-2-piperidinoethanol a. To a well-stirred mixture of 283 g of aluminium chloride in 1150 ml of anhydrous chloroform, 180 g of acetyl chloride are slowly added at a temperature of 0°–10°C, then 520 g of 4-n-butylthio-3-methylbenzene. The mixture is allowed to return to room temperature, then is hydrolysed by addition of ice and hydrochloric acid. After usual treatment, 324 g of 4-n-butylthio-3-methylacetophenone are obtained BP: 164°–166° (2 mm); n$_D^{25}$ = 1.5763; Yield: 82%.

b. By bromination of the preceding product with bromine in anhydrous ether, 4-n-butylthio-3-methyl-α-bromoacetophenone is obtained. MP (°C): 59.5°–60.5°(isopropanol).

c. The product obtained in the preceding operation is treated with 2 equivalents of piperidine (solvent: anhydrous ether; 18 hours at room temperature). Piperidine hydrobromide is filtered and washed with ether; after evaporation of the solvent, homogeneity of α-piperidino-4-n-butylthio-3-methylacetophenone obtained is tested by thin layer chromatography and said product is used as such in the following operation.

d. The reduction of the preceding production with sodium borohydrure in methanol at 0°C gives 1-(4-n-butylthio-3-methylphenyl)-2-piperidinoethanol. MP (°C): 157°–159° (MeOH-ether).

Centisimal analysis

% Calc.: C: 62.86 H: 8.79 N: 4.07 % Found : C: 62.98 H; 8.77 N: 3.90

Example 5

1-(3-Methyl-4-methylthiophenyl)-2-isopropylaminoethanol 11.8 g of α-isopropylamino-3-methyl-4-methylthioacetophenone (0.05 mol) in 100 cc of methanol are treated with 3.8 g of NaBH$_4$ (0.2 mol), the temperature being maintained at 0°–10°. Stirring is still continued for one hour at this temperature, then the solvent is evaporated under vacuum. The mixture is treated with water, then extracted with ether. The organic phase is dried on MgSO$_4$ and evaporated. 9.6 g (Yield of 81.3%) of free base are obtained, which can be recrystallised from a mixture ether-petroleum ether. Melting point: 89.5°–90.5°. 1(3-Methyl-4-methylthiophenyl)-2-isopropylaminoethanol hydrochloride is obtained by passing dry gaseous HCl through an ethereal solution of the free base and recrystallised from a methanol-ether mixture. Melting point: 154.5°–155.5°C.

Analysis

% Calc.: C: 56.58 H: 8.04 N: 5.08 % Found: C: 56.52 H: 8.04 N: 5.28

Example 6

1-(4-n-Butylthio-3-methylphenyl)-2-cyclohexylaminoethanol

To 5.7 g (0.0158 mol) of α-cyclohexylamino-4-n-butylthio-3-methylacetophenone HCl in 50 cc of methanol, 1.2 g of NaBH$_4$ are slowly added at a temperature of 0°–10°. Stirring is still continued for 2 hours at room temperature, then the solvent is evaporated under vacuum, water is added and extraction is made with ether. The ethereal phase is dried on MgSO$_4$ and after filtration and passage of dry gaseous HCl, 4.2 g of 1-(4-n-butylthio-3-methylphenyl)-2-cyclohexylaminoethanol HCl are obtained which are recrystallised from ethyl acetate. Melting point: 135.5°–136.5°C.

Analysis

% Calc.: C: 63.75 H: 9.01 N: 3.91 % Found: C: 63.78 H: 8.90 N: 3.83

II. EXAMPLES OF PREPARATION ACCORDING TO PROCESS B

Example 7

1-(3-Methyl-4-methylthiophenyl)-2-N,N-dipropylaminoethanol a. 55 g of 3-methyl-4-methylthio-α-bromoacetophenone in 200 ml of isopropanol and 125 g of aluminium isopropoxide in 300 ml of isopropanol are refluxed separately.

Both solutions are mixed and reflux is continued for 15 minutes. Then one cools and acidifies with 50% hydrochloric acid in the presence of ice. The precipitate obtained is filtered and washed with water. After drying, 50.8 g of 1-(3-methyl-4-methylthiophenyl)-2-bromoethanol are obtained. MP (°C): 74°–76°; Yield: 92%. The product can be recrystallised from cyclohexane. MP (°C): 78°–79°.

Centesimal analysis

% Calc.: C: 45.99 H: 5.02 % Found: C: 45.95 H: 5.05 b. To 13 g of 1-(3-methyl-4-methylthiophenyl)-2-bromoethanol in 50 ml of ethanol, 4.2 g of KOH in 25 ml of ethanol are added. The mixture is stirred for 30 minutes at room temperature, then the salt formed is filtered.

Dilution is made with an equal volume of water and extraction is carried out with ether. The organic phase is dried on magnesium sulfate, then evaporated. The only residue is used as such in the following operation.

c. To 6.5 g of 3-methyl-4-methylthiophenylethylene oxide in 50 ml of ethanol, 15 g of di-n-propylamine are added and one refluxes overnight. The solvent and excess of amine are evaporated under vacuum. The oily residue is taken up with ether and treated with dry gaseous HCl.

The resulting oil is treated with acetone, then with ethyl acetate. The product obtained is recrystallised from isopropanol. MP (°C): 161°–162°.

Centesimal analysis

% Calc.: C: 60.44 H: 8.88 N: 4.41 % Found: C: 60.30 H: 8.85 N: 4.28

Example 8

1-(3-Methyl-4-methylthiophenyl)-2-(α α-dimethylphenylethylamino) ethanol.

a. 20 g of 1-(3-methyl-4-methylthiophenyl)-2-bromo-ethanol in 100 ml of methanol are treated with 1.5 equivalent of NaOH in 30 ml of methanol. The mixture is stirred for 30 minutes at room temperature, then diluted with water. The product is extracted with ether, dried on MgSO$_4$ and the solvent is evaporated under vacuum. The epoxide obtained, the homogeneity of which is tested by thin layer chromatography is used as such in the following operation.

b. The oil obtained in the preceding operation, 50 ml of methanol and 20 g of α,α-dimethylphenylethylamine are refluxed for 48 hours. The solvent and excess of amine are evaporated under vacuum. The only residue is taken up with ether and extracted with 20% HCl. The aqueous phase is basified with 50% NaOH and extracted with ether. The ethereal phase is dried on MgSO$_4$, then evaporated; the residual oil crystallises in refrigerator, it is treated with diisopropyl ether and 5 g of product are isolated. MP (°C): 99°–100°; hydrochloride: MP (°C): 144°–145.5°

Centesimal analysis (free base)

% Calc.: C: 72.90 H: 8.26 N: 4.25 % Found: C: 72.70 H: 8.30 N: 4.05

Example 9

1-(4-Ethylthio-3-methylphenyl)-2-cyclopentylaminoethanol hydrochloride a. 4-Ethylthio-3-methylacetophenone is prepared by action of acetyl chloride and aluminium chloride in chloroform on 1-ethylthio-2-methylbenzene according to already described processes. BP: 117°–119°C (0.25 mm).

b. The 4-ethylthio-3-methyl-α-bromoacetophenone is obtained by bromination of the preceding product with bromine in anhydrous ether. MP (°C): 72°–73°.

c. The 1-(4-ethylthio-3-methylphenyl)-2-bromoethanol is obtained by reduction of the preceding product with aluminium isopropoxide in isopropanol. MP (°C): 74°–75°.

d. 5.5 g (0.02 M) of 1-(4-ethylthio-3-methylphenyl)-2-bromoethanol and 13.2 g (0.12 M) of cyclopentylamine are dissolved in 100 ml of absolute ethanol. The solution is maintained at reflux for 24 hours. The solution is concentrated to one fourth of its initial volume and poured in a 1N hydrochloric acid solution. The aqueous phase is extracted with ether (3 × 15 ml) and made alkaline with a saturated solution of sodium carbonate and re-extracted with ether (3 × 30 ml).

The ethereal phase is dried on MgSO$_4$ and dry evaporated. Excess of cyclopentylamine is driven away at reduced pressure; the residue is taken up in anhydrous ether. 4.5 g of 1-(4-ethylthio-3-methylphenyl)-2-cyclopentylaminoethanol hydrochloride are obtained by passing a stream of anhydrous hydrochloric acid. Yield: 75 %; MP (°C): 123°–124°. This derivative crystallises from methanol-ether.

Centesimal analysis

% Calc.: C: 60.80 H: 8.30 N: 4.40 % Found: C: 60.60 H: 8.15 N: 4.30

Example 10

1-(3-Chloro-4-methylthiophenyl)-2-isopropylaminoethanol 1. 13.9 g (0.05 mol) of α-bromo-3-chloro-4-methylthioacetophenone in 150 cc of isopropanol and 30.6 g of aluminium isopropoxide (0.15 mol) in 200 cc of isopropanol are refluxed separately. The two solutions are mixed and reflux is continued for 30 minutes. After cooling, the product is poured in a mixture of water and ice and acidified with 20% HCl. The solid is filtered and dried. 10 g of 1-(3-chloro-4-methylthio-phenyl)-2-bromoethanol are obtained. Yield: 71.4%; melting point: 86°–87°C.

2. 7 g of 1-(3-chloro-4-methylthiophenyl)-2-bromoethanol (0.025 mol) in 50 cc of ethanol are treated with 1.4 g of sodium hydroxide (0.035 mol). The product is stirred for 10 minutes, then diluted with water. One extracts with ether and dries on magnesium sulfate. The solvent is evaporated under vacuum and the residual oil is treated with 100 cc of EtOH and 5.9 g of isopropylamine (0.1 mol). The product is brought to 50° overnight with stirring. The solvent and excess of isopropylamine are evaporated under vacuum. The residual oil crystallises after some time (melting point of 111°–112°C after recrystallisation from cyclohexane). The free base is dissolved in ether; by passing dry gaseous HCl, 4.88 g of 1-(3-chloro-4-methylthiophenyl)-2-isopropylaminoethanol hydrochloride are obtained which are recrystallised from a methanol-ether mixture. Melting point: 139°–141°C.

Analysis

% Calc.: C: 55.48 H: 6.98 N: 5.39 % Found: C: 55.47 H: 6.91 N: 5.27

Example 11

1-(3-Methyl-4-methylthiophenyl)-2-isopropylaminoethanol

1. To 26.1 g (0.1 mol) of 1-(3-methyl-4-methylthiophenyl)-2-bromoethanol in 150 cc of ethanol, 7.8 g (0.15 mol) of potassium hydroxide in 100 cc of ethanol are added. The mixture is stirred for 15 minutes at room temperature and the salt formed is filtered. The mixture is diluted with water and several times extracted with ether. The organic phase is dried on MgSO$_4$ and the solvent is evaporated under vacuum. The yellow oil obtained is directly used in the following operation.

2. To 5.7 g of 3-methyl-4-methylthiophenylethylene oxide in 30 cc of isopropanol, 7.6 g of isopropylamine are added. The solution is refluxed overnight. The solvent and excess of amine are evaporated under vacuum. The oil obtained crystallises a little moment later. 12.1 g of 1-(3-methyl-4-methylthiophenyl)-2-isopropylaminoethanol are obtained (yield of 61 %) which are recrystallised from cyclohexane. Melting point: 89.5°–90.5°. The hydrochloride is recrystallised from a methanol-ether mixture; melting point: 154°–155.5°C.

Analysis

% Calc.: C: 56.58 H: 8.04 N: 5.08 % Found: C: 56.52 H: 8.04 N: 5.28

III. EXAMPLES OF PREPARATION ACCORDING TO PROCESS C

Example 12

1-(3-Methyl-4-isopropylthiophenyl)-2-n-octylaminoethanol hydrochloride a. The 3-methyl-4-isopropylthioacetophenone is obtained by action of acetyl chloride and aluminium chloride in chloroform on 1-methyl-2-isopropylthiobenzene according to a conventional process already previously described. BP: 111°–114°C (0.5 mm).

b. The 3-methyl-4-isopropylthio-α-bromoacetophenone is obtained by bromination of the preceding product with trimethylaniline tribromide in tetrahydrofuran at 0°C. MP (°C): 40°–41°.

Centesimal analysis

% Calc.: C: 50.20 H: 5.25 % Found: C: 50.05 H: 5.15 c. The 3-methyl-4-isopropylthiophenylglyoxal is obtained by action of dimethyl sulfoxide on the preceding product (36 hours at room temperature). Homogeneity of the compound obtained is tested by thin layer chromatography before to use it in the following operation.

d. 240 g (1 M) of 3-methyl-4-isopropylthiophenylglyoxal, 780 g (6 M) of n-octylamine and 1 liter of anhydrous methanol are stirred for half a hour at room temperature. The solution is cooled to 0°C and 114 g (3 M) of sodium borohydride are added over half a hour. The solution is then maintained at 20°C for 3 hours.

The solution is concentrated to one tenth of its initial volume and poured into a 1 N hydrochloric acid solution. The aqueous phase is extracted with ether (3 × 40 ml) and alkalinised with a 1 N sodium hydroxide solution and re-extracted with ether (3 × 60 ml).

The ethereal phase is dried on magnesium sulfate and dry evaporated. Excess of n-octylamine is eliminated at a reduced pressure. The residue is taken up in anhydrous ether. By passing a gaseous and dry stream of hydrochloric acid, 153 g of 1-(3-methyl-4-isopropylthiophenyl)-2-n-octylaminoethanol hydrochloride are obtained. Yield: 40%; MP (°C): 169°.

Centesimal analysis

% Calc.: C: 64.30 H: 9.70 N: 3.75 % Found: C: 64.20 H: 9.70 N: 3.60

Example 13

1-(3-Methoxy-4-methylthiophenyl)-2-tertbutylaminoethanol hydrochloride a. The 3-methoxy-4-methylthioacetophenone is obtained by action of acetyl chloride and aluminium chloride on 1-methoxy-2-methylthiobenzene (solvent CHCl$_3$ — 2 hours at room temperature). BP: 160° (2 mm).

Centesimal analysis

% Calc.: C: 61.20 H: 6.15 % Found: C: 60.90 H: 5.95

The acetylation position is verified by examination of the nuclear magnetic resonance spectrum.

b. The 3-methoxy-4-methylthio-α-bromoacetophenone is obtained by bromination of the preceding product in ether according to a technique already described. MP (°C): 67°–68°.

Centesimal analysis

% Calc.: C: 43.65 H: 4.05 % Found: C: 43.45 H: 3.95 c. The 3-methoxy-4-methylthiophenylglyoxal is obtained by action of dimethyl sulfoxide on the preceding product (48 hours at room temperature). The purity of the product is tested by thin layer chromatography and is used as such in the following operation.

d. 13.2 g (0.06 M) of 3-methoxy-4-methylthiophenylglyoxal, 27 g (0.36 M) of tertbutylamine and 50 ml of anhydrous methanol are stirred for 30 minutes at room temperature. The solution is cooled to 0°C and a small portion of 6.8 g (0.18 M) of sodium borohydride is added. The solution is brought to room temperature and maintained 2 hours at this temperature, then it is concentrated to one tenth of its initial volume and poured into a 1 N hydrochloric acid solution.

The aqueous phase is extracted with ether (3 × 15 ml), then rendered alkaline with a 1 N sodium hydroxide solution and re-extracted with ether (3 × 35 ml). The ethereal phase is dried on magnesium sulfate and dry evaporated. The residue is dissolved in anhydrous ether and by passing a stream of anhydrous hydrochloric acid, 12.3 g of 1-(3-methoxy-4-methylthiophenyl)-2-tertbutyl-aminoethanol hydrochloride are obtained, which are recrystallised from a methanol-ether mixture. Yield: 60%; MP (°C): 192°–193°.

Centesimal analysis

% Calc.: C: 54.95 H: 7.90 N: 4.55 % Found: C: 54.90 H: 7.85 N: 4.45

Example 14

1-(3-Methyl-4-methylsulfonylphenyl)-2-isopropylaminoethanol a. 3-Methyl-4-methylsulfonylacetophenone This product is obtained by oxidation of 3-methyl-4-methylthioacetophenone with hydrogen peroxide in acetic acid. Yield: 90%; MP (°C): 67-68 (cyclohexane).

b. 3-Methyl-4-methylsulfonyl-α-bromoacetophenone

Obtained by bromination of the preceding product with bromine in acetic acid. Yield: 88%; MP (°C): 102°–104° (benzene).

c. 3-Methyl-4-methylsulfonylphenylglyoxal

Obtained by action of dimethyl sulfoxide on the preceding product (48 hours at room temperature). Homgeneity of the product is tested by thin layer chromatography.

d. 1-(3-Methyl-4-methylsulfonylphenyl)-2-isopropylaminoethanol

To 7 g of the preceding product (0.03 M) and 10.8 g of isopropylamine (0.18 M) in 100 ml of methanol, 3 g of sodium borohydride are slowly added at a temperature of 0°–10°C while agitating. Agitation is continued for 3 hours at this temperature then the solvent and excess of amine are evaporated under vacuum. The residue is treated with water and extracted with ether. The organic phase is dried on MgSO₄ and by passing of dry gaseous hydrochloric acid; 3.2 g of product are obtained, which is purified by recrystallisation from isopropanol. MP (°C): 182°–183°.

Centesimal analysis

% Calc: C: 50.72 H: 7.20 N: 4.55 % Found: C: 50.55 H: 7.30 N: 4.35

Example 15

1-(3-Chloro-4-methylthiophenyl)-2-N-(1-phenyl-2-aminopropanol) ethanol a. To 93 g of aluminium chloride in 380 ml of anhydrous chloroform, 60 g of acetyl chloride are added, then slowly 92 g of o-chlorothioanisole, the temperature being maintained at 10°. The product is still stirred for 2 hours at room temperature, then by the usual treatment 97.2 g of 3-chloro-4-methylthio-acetophenone are obtained. BP = 142–146 (0.7 mm). MP (°C): 49.5–50.5; Yield: 83.6%.

b. To 52 g of 3-chloro-4-methylthioacetophenone in 250 ml of anhydrous ether, 41.6 g of bromine are added, while maintaining the temperature at 20° and passing a slight stream of nitrogen through the solution. Then 200 ml of petroleum ether are added and the solid obtained is filtered and washed with a 10% aqueous bicarbonate solution. After drying, 60.4 g of 3-chloro-4-methylthio-α-bromoacetophenone are obtained. MP (°C): 84°–86°; Yield: 83.5%.

c. 28 g of 3-chloro-4-methylthio-α-bromoacetophenone and 215 ml of dimethyl sulfoxide are stirred for 36 hours at room temperature. The solution is poured onto ice and extracted with ether. The organic phase is dried on MgSO₄, then the solvent is evaporated under vacuum. 22.1 g of a yellow oil are obtained, which crystallises rapidly.

The 3-chloro-4-methylthiophenylglyoxal, the homogeneity of which is tested by thin layer chromatography, is used as such in the following operation.

d. To 7 g of 3-chloro-4-methylthiophenylglyoxal (0.033 M) in 50 ml of ethanol, 37.4 g of 1-phenyl-2-aminopropanol hydrochloride (0.2 M) are added, then slowly 4.4 g of sodium borohydride while stirring and cooling in water-bath. The product is still stirred overnight at room temperature, then alcohol and excess of amine are evaporated under vacuum. The residue is taken up in water and extracted with ether. The organic phase is washed with water, then dried on MgSO₄. By passing a stream of dry gaseous HCl, 2.7 g of hydrochloride are obtained. Yield: 33%. An analytical sample is recrystallised from a methanol-ether mixture. MP (°C): 212.5°–213.5°.

Centesimal analysis

% Calc.: C: 55.67 H: 5.97 N: 3.61 % Found: C: 55.85 H: 5.75 N: 3.45

Example 16

1-(3-Methyl-4-methylthiophenyl)-2-secbutylaminoethanol

To 12.7 g (0.06 M) of 3-methyl-4-methylthiophenylglyoxal and 21.9 g of sec-butylamine in 100 ml of methanol cooled to 10°C, 6.8 g of sodium borohydride are slowly added. The solution is then brought to room temperature and maintained for 2 hours at said temperature. The solution is concentrated to one fourth of its initial volume and acidified with 1 N HCl. The aqueous phase is washed with ether, then alkalinised with 20% Na₂CO₃. The product is extracted with ether, dried on MgSO₄ and evaporated. The oily residue is taken up with anhydrous ether and 1-(3-methyl-4-methylthiophenyl)-2-secbutylaminoethanol hydrochloride is obtained by passing a stream of dry gaseous HCl. MP (°C): 123°–124° (MeOH-ether)

Centesimal analysis

% Calc.: C: 58.00 H: 8.20 N: 4.65 % Found: C: 57.90 H: 8.20 N: 4.55

Example 17

1-(3-Ethyl-4-methylthiophenyl)-2-isopropylaminoethanol 20.6 g of 3-ethyl-4-methylthiophenylglyoxal (0.1 M) and 17.7 g of isopropylamine in 100 ml of methanol are hydrogenated in the presence of 0.1 g of platinum oxide (normal pressure and temperature). The solvent and excess of amine are evaporated under vacuum. The residue is taken up in anhydrous ether and the hydrochloride is obtained by passing dry gaseous HCl. MP (°C): 109°–110° (MeOH - ether).

Centesimal analysis

% Calc.: C: 58.05 H: 8.35 N: 4.80 % Found: C: 58.05 H: 8.40 N: 4.75

Example 18

1-(3-Ethyl-4-methylthiophenyl)-2-secbutylaminoethanol 10.3 g of 3-ethyl-4-methylthiophenylglyoxal (0.05 M) and 10.95 g of secbutylamine in 100 ml of absolute ethanol are hydrogenated at normal pressure and temperature in the presence of 0.1 g of platinum oxide. The solvent and excess of amine are evaporated under vacuum. The residue is taken up in anhydrous ether and 10.6 g of hydrochloride are obtained by passing gaseous HCl (Yield: 71%). MP (°C): 108-109 (MeOH - ether).

Centesimal analysis

% Cal.: C: 59.30 H: 8.60 N: 4.60 % Found: C: 59.15 H: 8.65 N: 4.50

Example 19

1-(4-n-Butylthio-3-methylphenyl)-2-(3-methoxypropylamino)ethanol

To 11.8 g of 4-n-butylthio-3-methylphenylglyoxal (0.05 M) and 26.5 g of 3-methoxypropylamine in 80 ml of methanol, 4.8 g of sodium borohydride are slowly added at a temperature of 0°-5°C. After addition, the product is allowed to come back to room temperature and is still stirred for 2 hours. Isolation of the product is made in a way already previously described. 10.4 g of hydrochloride are obtained (Yield: 62%). MP (°C): 109°-110° (benzene-petroleum ether).

Centesimal analysis

% Calc.: C: 58.87 H: 8.69 N: 4.02 % Found: C: 58.59 H: 8.55 N: 3.95

IV. Examples of preparation according to Process D

Example 20

1-(3-Methyl-4-methylthiophenyl)-2-(1.2-dimethylpropylamino) ethanol hydrochloride a. 259 g (1 M) of α-bromo-3-methyl-4-methylthioacetophenone are dissolved in 1500 ml of chloroform. 140 g (1 M) of hexamethylene tetramine are added and the solution is maintained with stirring for 2 hours at ordinary temperature. The adduct is filtered and washed with water, then with acetone. 248 g are obtained. Yield: 60%.

b. 411 g (1 M) of the adduct are dissolved in 900 ml of ethanol containing 450 ml of concentrated hydrochloric acid. The solution is stirred overnight at ordinary temperature. The ammonium chloride is filtered, washed with ethyl alcohol. The filtrate is dry evaporated. 186 g of α-amino-3-methyl-4-methylthioacetophenone hydrochloride (Yield: 80%) are isolated, which are recrystallised from a methanol-ether mixture.

c. 116 g (0.5 M) of α-amino-3-methyl-4-methylthioacetophenone hydrochloride are dissolved in 1 liter of methanol. The solution is cooled to 0°C and 39 g (1 M) of sodium borohydride are added over 15 minutes. The solution brought to ordinary temperature is stirred for 2 hours. The solution is concentrated to the tenth of its initial volume, poured into water, then made alkaline with a 1 N sodium hydroxide solution and extracted with ether.

The ethereal phase is dried on MgSO$_4$ and dry evaporated. 54 g of 1-(3-methyl-4-methylthiophenyl)-2-aminoethanol are isolated. The hydrochloride is obtained by passing dry gaseous hydrochloric acid through an ethereal solution of the base; it is recrystallised from a methanol-ether mixture. MP (°C): 187°-188°.

Centesimal analysis

% Calc.: C: 51.40 H: 6.90 N: 6.00 % Found: C: 51.30 H: 6.85 N: 5.80 d. 19.7 g of 1-(3-methyl-4-methylthiophenyl)-2-aminoethanol (0.1 M) are dissolved in 50 ml of methylisopropylketone. The solution is refluxed for 5 hours. Excess of ketone is distilled and the residue is dissolved in 30 ml of methanol. To this solution cooled to 0°C, 0.8 g (0.2 M) of sodium borohydride are added over 15 minutes. The solution is brought to normal temperature, then after 2 hours is concentrated to the fourth of its initial volume and the residue is poured into water. One alkalinises with a 20% NaOH solution and extracts with ether. The ethereal phase is dried on MgSO$_4$. By passing a stream of dry gaseous HCl, 15 g of 1-(3-methyl-4-methylthiophenyl)-2-(1.2-di-methylpropylamino)ethanol hydrochloride are obtained. MP (°C): 177°-178° (methanol-ether).

Centesimal analysis

% Calc.: C: 59.30 H: 8.60 N: 4.60 % Found: C: 59.00 H: 8.45 N: 4.45

Example 21

1-(3-Methyl-4-methylthiophenyl)-2-isopropylaminoethanol hydrochloride 19.7 g (0.1 M) of 1-(3-methyl-4-methylthiophenyl)-2-aminoethanol are dissolved in 50 ml of acetone. The solution is refluxed for 5 hours. The acetone is distilled and the residue is dissolved in 30 ml of methanol. To this solution cooled to 0°C, 0.8 g (0.2 M) of sodium borohydride are added over 15 minutes. The solution is brought to room temperature and maintained for 2 hours at this temperature. The solution is concentrated to the fourth of its initial volume and poured into water. The aqueous phase is made alkaline with a sodium hydroxide solution and extracted with ether. The ethereal phase is dried on MgSO$_4$. By passing a stream of dry gaseous hydrochloric acid, 11 g of 1-(3-methyl-4-methylthiophenyl)-2-isopropylaminoethanol hydrochloride are obtained. Yield: 40 %; MP (°C): 154.5°-155.5°.

Centesimal analysis

% Calc.: C: 56.58 H: 8.04 N: 5.08 % Found: C: 56.60 H: 8.10 N: 5.10

V. Example of preparation according to Process E

Example 22

1-(4-n-Butylthio-3-methylphenyl)-2-N,N-dipropylaminoethanol

To 3.8 g of lithium aluminium hydride (0.1 M) in 50 ml of anhydrous ether, 3.37 g of N,N-dipropyl-4-n-butylthio-3-methylmandelamide (0.1 M) in 50 ml of anhydrous ether are slowly added while stirring. After addition, the product is still stirred for 30 minutes at room temperature, then 3.3 ml of water and 3.3 ml of an aqueous solution of sodium hydroxide, then 10 ml of water are slowly added. After filtration, the organic phase is dried on MgSO$_4$. By passing a stream of dry gaseous hydrochloric acid, 2.44 g of 1-(4-n-butylthio-3-methylphenyl)-2-N,N-dipropylamino-ethanol hydrochloride are obtained. Yield: 72 %. MP (°C): 144°–145° (acetone-petroleum ether).

Centesimal analysis

% Calc.: C: 63.39 H: 9.52 N: 3.89 % Found: C: 63.21 H: 9.62 N: 3.67

VI. Particulars examples of preparation of amino-alcohol salts

Example 23

1-(3-Methyl-4-methylthiophenyl)-2-isopropylaminoethanol oxalate

To 1.20 g of 1-(3-methyl-4-methylthiophenyl)-2-isopropylaminoethanol in 40 ml of ether, 0.45 g of oxalic acid in 50 ml of ether are dropwise added while stirring. The precipitate is filtered and washed with ether, then crystallised from a methanol-ether mixture. MP (°C): 165.5° – 167.5°.

1-(3-Methyl-4-methylthiophenyl)-2-isopropylaminoethanol gluconate

To 1.20 g of 1-(3-methyl-4-methylthiophenyl)-2-isopropylaminoethanol in 40 ml of water, 1.96 ml of a 50% gluconic acid solution are added. The mixture is heated in water-bath during 1 hour at 70°, then the solution is lyophilised (2.18 g of the salt obtained are soluble in 5 ml of water and give a pH of 4.6).

Example 24

1-(3-Methyl-4-methylthiophenyl)-2-isopropylaminoethanol lactate

To 1.2 g of 1-(3-methyl-4-methylthiophenyl)-2-isopropylaminoethanol in 32 ml of water, 0.53 g of a 85% aqueous lactic acid solution are added. The product is heated in a water-bath for 2 hours at 50°, then the solution is lyophilised. (1.55g of the salt obtained are soluble in 5 ml of water).

The Table hereinbefore announced and relating to compounds prepared in the same way as compounds of precited detailed examples is given hereinafter, as Tables I and II.

Table I groups compounds presenting in general formula I, for $R_3$ and $R_4$, a hydrogen atom, while Table II relates to compounds wherein $R_3$ and/or $R_4$ are not hydrogen.

TABLE I $R_3=R_4=H$

| No | $R_1$ | $R_2$ | $-N\begin{smallmatrix}R_5\\R_6\end{smallmatrix}$ | M.P., °C | Formula | C, % Calc. | C, % Found | H, % Calc. | H, % Found | N, % Calc. | N, % Found |
|---|---|---|---|---|---|---|---|---|---|---|---|
| 1 | H- $C_4H_9S$- | 3CH$_3$ | -NH-CH$_2$-CH=CH$_2$ | 126-128 (acetone) | $C_{16}H_{25}NOS$.HCl | 60.83 | 60.90 | 8.29 | 8.30 | 4.43 | 4.22 |
| 2 | CH$_3$S- | 3Cl | -NH-(CH$_2$)$_3$OCH$_3$ | 124-126 (MeOH-ether) | $C_{13}H_{20}ClNO_2S$. HCl | 47.85 | 47.80 | 6.49 | 6.30 | 4.29 | 4.15 |
| 3 | CH$_3$S- | 3Cl | -NH-(CH$_2$)$_3$-N◯O | 251.5-252.5 (MeOH) | $C_{16}H_{25}ClN_2O_2S$. 2HCl | 45.99 | 45.95 | 6.51 | 6.45 | 6.70 | 6.85 |
| 4 | CH$_3$S- | 3Cl | -NH-(CH$_2$)$_3$OH | 94-95 (acetone) | $C_{12}H_{19}ClNO_2S$ | 52.26 | 52.05 | 6.58 | 6.70 | 5.08 | 4.85 |
| 5 | CH$_3$S | 3Cl | -NH-(CH$_2$)$_2$N(C$_2$H$_5$)$_2$ | 176.5-178 (MeOH-ether) | $C_{15}H_{25}ClN_2OS$. 2HCl | 46.21 | 45.99 | 6.98 | 6.80 | 7.18 | 7.10 |
| 6 | CH$_3$S | 3CH$_3$ | -NH-CH-CH$_2$O-◯<br>　　　CH$_3$ | 132-133 (acetone) | $C_{19}H_{25}NO_2S$. HCl | 62.02 | 61.89 | 7.12 | 7.25 | 3.80 | 3.72 |
| 7 | CH$_3$S- | 3CH$_3$ | -NH-CH-(CH$_2$)$_2$-◯<br>　　　CH$_3$ | 158-159 (MeOH-ether) | $C_{20}H_{27}NOS$. HCl | 65.65 | 65.50 | 7.70 | 7.65 | 3.80 | 3.60 |
| 8 | CH$_3$S- | 3CH$_3$ | -NH-CH-CH$_2$-◯<br>　　　CH$_3$ | 157-158.5 (MeOH-ether) | $C_{19}H_{25}NOS$. HCl | 64.85 | 64.55 | 9.30 | 9.40 | 4.05 | 4.05 |
| 9 | CH$_3$S- | 3F | -NHisoC$_3$H$_7$ | 124-125 (MeOH-ether) | $C_{12}H_{18}FNOS$. HCl | 51.50 | 51.30 | 6.85 | 6.90 | 5.00 | 5.00 |
| 10 | n-$C_4H_9S$- | 3CH$_3$ | -NH-(CH$_2$)$_3$OCH$_3$ | 109-110 ($C_6H_6$-ether of p.) | $C_{17}H_{29}NO_2S$. HCl | 58.87 | 58.59 | 8.69 | 8.55 | 4.02 | 3.95 |
| 11 | n-$C_4H_9S$- | 3CH$_3$ | -NH-CH-CHOH-◯<br>　　CH$_3$ | 158-159 (isoProH) | $C_{22}H_{31}NO_2S$. HCl | 64.45 | 64.25 | 7.87 | 7.65 | 3.42 | 3.15 |
| 12 | iso-$C_4H_9S$- | 3CH$_3$ | -NHisoC$_3$H$_7$ | 123-125 (acetone) | $C_{16}H_{27}NOS$. HCl | 60.45 | 60.50 | 8.88 | 8.90 | 4.41 | 4.35 |
| 13 | iso-$C_4H_9S$- | 3CH$_3$ | -NH-(CH$_2$)$_7$-CH$_3$ | 175-177 (acetone) | $C_{21}H_{37}NOS$. HCl | 65.00 | 65.05 | 9.87 | 9.75 | 3.61 | 3.50 |
| 14 | n- | 3CH$_3$ | -NH-C(CH$_3$)$_3$ | 129-130 | $C_{18}H_{31}NOS$. | 62.49 | 62.40 | 9.32 | 9.20 | 4.05 | 3.90 |

TABLE I-continued

Structure: Ar-CHOH-CH(R4)-N(R5)(R6), where Ar is phenyl with substituents R1 (position 4), R2 (3 positions: 3,5,6 via 3CH3 notation), R3

$R_3 = R_4 = H$

| No | R₁ | R₂ | -N(R₅)(R₆) | M.P., °C (solvent) | Formula | C % Calc. | C % Found | H % Calc. | H % Found | N % Calc. | N % Found |
|---|---|---|---|---|---|---|---|---|---|---|---|
| 15 | n-C₅H₁₁S- | 3CH₃ | -NH-(CH₂)₃-CH₃ | 192-195 (MeOH-ether) | C₁₈H₃₁NOS·HCl | 62.49 | 62.50 | 9.32 | 9.55 | 4.05 | 4.30 |
| 16 | n-C₅H₁₁S- | 3CH₃ | -NH-isoC₃H₇ | 109-110 (acetone) | C₁₈H₃₁NOS·HCl | 61.89 | 61.72 | 8.55 | 8.65 | 4.24 | 4.00 |
| 17 | n-C₆H₁₃S- | 3CH₃ | -NH-(CH₂)₃-CH₃ | 205-207 (MeOH-ether) | C₁₉H₃₃NOS·HCl | 63.74 | 63.50 | 9.01 | 9.07 | 3.91 | 3.85 |
| 18 | n-C₆H₁₃S- | 3CH₃ | -NH-(CH₂)₂-CH₃ | 178-179 (acetone) | C₁₈H₃₁NOS·HCl | 62.86 | 63.02 | 8.79 | 8.81 | 4.07 | 3.95 |
| 19 | n-C₆H₁₃S- | 3CH₃ | -NHisoC₃H₇ | 114-116 (acetone) | C₂₀H₃₅NOS·HCl | 64.22 | 64.45 | 9.70 | 9.85 | 3.71 | 3.85 |
| 20 | n-C₈H₁₇S- | 3CH₃ | -NH-(CH₂)₃-CH₃ | 201.5-203 (acetone) | C₂₁H₃₇NOS·HCl | 65.00 | 65.15 | 9.87 | 9.90 | 3.61 | 3.55 |
| 21 | n-C₈H₁₇S- | 3CH₃ | -NHsecC₄H₉ | 76.5-78 (acetone) | C₂₁H₃₇NOS·HCl | 65.00 | 64.85 | 9.87 | 9.75 | 3.61 | 3.35 |
| 22 | n-C₈H₁₇S- | 3CH₃ | -NH-C(CH₃)₃ | 107-108.5 (MeOH-ether) | C₂₁H₃₇NOS·HCl | 65.00 | 64.88 | 9.87 | 10.08 | 3.61 | 3.55 |
| 23 | n-C₁₀H₂₁S- | 3CH₃ | -NH-C(CH₃)₃ | 107-109 (Ac.ethyl) | C₂₃H₄₁NOS·HCl | 66.39 | 66.45 | 10.17 | 10.20 | 3.37 | 3.30 |
| 24 | n-C₁₀H₂₁S- | 3CH₃ | -NHsecC₄H₉ | 70-72.5 (Ac.ethyl) | C₂₃H₄₁NOS·HCl | 66.39 | 66.35 | 10.17 | 10.00 | 3.37 | 3.30 |
| 25 | n-C₁₀H₂₁S- | 3CH₃ | -NHisoC₃H₇ | 116-118 (Ac.ethyl) | C₂₂H₃₉NOS·HCl | 65.72 | 65.65 | 10.03 | 10.05 | 3.48 | 3.30 |
| 26 | n-C₁₀H₂₁S- | 3CH₃ | -NH-(CH₂)₇-CH₃ | 168-171 (acetone) | C₂₇H₄₉NOS·HCl | 68.68 | 68.65 | 10.67 | 10.70 | 2.97 | 2.85 |
| 27 | CH₃S- | 2Cl | -NHisoC₃H₇ | 182-184 (MeOH-ether) | C₁₂H₁₈ClNOS·HCl | 55.47 | 55.27 | 6.98 | 6.79 | 5.39 | 5.41 |
| 28 | CH₃S- | 2Cl | -NHsecC₄H₉ | 150-152 (acetone) | C₁₃H₂₀ClNOS·HCl | 50.32 | 50.35 | 6.82 | 6.75 | 4.51 | 4.35 |
| 29 | CH₃S- | 2Cl | -NH-C(CH₃)₃ | 146.5-147.5 (acetone) | C₁₃H₂₀ClNOS·HCl | 50.32 | 50.20 | 6.82 | 6.80 | 4.51 | 4.40 |
| 30 | CH₃SO₂ | 3CH₃ | -NH-C(CH₃)₃ | 240-241.5 (MeOH-ether) | C₁₄H₂₃NO₃S·HCl | 52.24 | 52.15 | 7.51 | 7.30 | 4.35 | 4.15 |
| 31 | n-C₃H₇S- | 3CH₃ | -NHisoC₃H₇ | 99.5-100 (MeOH-ether) | C₁₅H₂₅NOS·HCl | 59.30 | 59.15 | 8.60 | 8.60 | 4.60 | 4.60 |
| 32 | n-C₃H₇S- | 3CH₃ | -NH-(CH₂)₃CH₃ | 192-193 (MeOH-ether) | C₁₆H₂₇NOS·HCl | 60.45 | 60.30 | 8.90 | 8.95 | 4.40 | 4.20 |
| 33 | n-C₃H₇S- | 3CH₃ | -NHsecC₄H₉ | 106-107 (MeOH-ether) | C₁₆H₂₇NOS·HCl | 60.45 | 60.25 | 8.90 | 9.05 | 4.40 | 4.35 |
| 34 | n-C₃H₇S- | 3CH₃ | -NH-(CH₂)₇-CH₃ | 184-186 (MeOH-ether) | C₂₀H₃₅NOS·HCl | 64.20 | 64.05 | 9.70 | 9.70 | 3.75 | 3.70 |
| 35 | iso-C₃H₇S- | 3CH₃ | -NH-C₆H₁₁ | 156-157 (MeOH-ether) | C₁₈H₂₉NOS·HCl | 62.85 | 62.45 | 8.80 | 8.65 | 4.05 | 4.00 |
| 36 | iso-C₃H₇S- | 3CH₃ | -NH-(CH₂)₃-CH₃ | 198-199 (MeOH-ether) | C₁₆H₂₇NOS·HCl | 60.45 | 60.40 | 8.90 | 8.80 | 4.40 | 4.30 |
| 37 | iso-C₃H₇S- | 3CH₃ | -NHsecC₄H₉ | 141-142 (MeOH-ether) | C₁₆H₂₇NOS·HCl | 60.45 | 60.20 | 8.90 | 8.90 | 4.40 | 4.40 |
| 38 | iso-C₃H₇S- | 3CH₃ | -NH-(CH₂)₆-CH₃ | 185-186 (MeOH-ether) | C₁₉H₃₃NOS·HCl | 63.40 | 63.15 | 9.50 | 9.35 | 3.90 | 3.75 |
| 39 | iso-C₃H₇S- | 3CH₃ | -NH-CH₂-CH₂-C₆H₅ | 185.5-186.5 (MeOH-ether) | C₂₀H₂₇NOS·HCl | 65.65 | 65.60 | 7.70 | 7.55 | 3.80 | 3.95 |
| 40 | C₂H₅S- | 3CH₃ | -NH-(CH₂)₂CH₃ | 142-144 (MeOH-ether) | C₁₄H₂₃NOS·HCl | 58.00 | 57.80 | 8.00 | 8.10 | 4.80 | 4.60 |
| 41 | C₂H₅S- | 3CH₃ | -NH-CH(CH₃)-CH₂-C₆H₅ | 135-136 (C₆H₆) | C₂₀H₂₇NOS·HCl | 64.65 | 64.70 | 7.70 | 7.60 | 4.00 | 4.05 |
| 42 | C₂H₅S- | 3CH₃ | -NH-(CH₂)₃-CH₃ | 180-183 (C₆H₆-CHCl₃) | C₁₅H₂₅NOS·HCl | 59.30 | 59.15 | 8.60 | 8.55 | 4.60 | 4.40 |
| 43 | C₂H₅S- | 3CH₃ | -NH-CH(CH₃)-CH₂-C₆H₅ | 125-126 (MeOH-ether) | C₂₀H₂₇NOS·HCl | 65.65 | 65.70 | 7.70 | 7.80 | 3.80 | 3.70 |
| 44 | C₂H₅S- | 3CH₃ | -NH-(CH₂)₇-CH₃ | 186-188 (MeOH-ether) | C₁₉H₃₃NOS·HCl | 63.40 | 63.25 | 9.50 | 9.35 | 3.90 | 3.60 |
| 45 | C₂H₅S- | 3CH₃ | -NH-C(CH₃)₃ | 200-201 (MeOH-ether) | C₁₅H₂₅NOS·HCl | 59.30 | 59.50 | 8.60 | 8.30 | 4.60 | 4.45 |
| 46 | CH₃S- | 3CH₃ | -NH-(CH₂)₉-CH₃ | 179-180 (MeOH-ether) | C₂₀H₃₅NOS·HCl | 64.20 | 64.15 | 9.70 | 9.70 | 3.70 | 3.60 |

TABLE I-continued

R₃=R₄=H

| No | R₁ | R₂ | -NR₅R₆ | M.P., °C⁽¹⁾ | Formula | C, % Calc. | C, % Found | H, % Calc. | H, % Found | N, % Calc. | N, % Found |
|---|---|---|---|---|---|---|---|---|---|---|---|
| 47 | CH₃S- | 3CH₃ | -NH-(CH₂)₆-CH₃ | 199-200 (MeoH-ether) | C₁₇H₂₉NOS. HCl | 61.50 | 61.15 | 9.10 | 9.20 | 4.20 | 4.05 |
| 48 | CH₃S- | 3CH₃ | -NH-CH-CH₂-CH(CH₃)₂ / CH₃ | 164-165 (MeoH-ether) | C₁₆H₂₇NOS. HCl | 60.45 | 60.00 | 8.90 | 8.80 | 4.40 | 4.30 |
| 49 | CH₃S- | 3CH₃ | -NH-(CH₂)₁₀-CH₃ | 141-142 (MeoH-ether) | C₂₁H₃₇NOS. HCl | 65.00 | 64.85 | 9.85 | 9.90 | 3.60 | 3.80 |
| 50 | CH₃S- | 3CH₃ | -NH-CH-CH₂-C₆H₃Cl₂ / CH₃ | 177-178 (MeoH-ether) | C₁₉H₂₃Cl₂NOS. HCl | 54.20 | 54.35 | 5.75 | 5.75 | 3.30 | 3.20 |
| 51 | CH₃S- | 3CH₃ | -NH-CH-CH₂-C₆H₄-CH₃ / CH₃ | 158-159 (MeoH-ether) | C₂₀H₂₇NOS. HCl | 65.65 | 65.75 | 7.70 | 7.70 | 3.80 | 3.70 |
| 52 | CH₃S- | 3CH₃ | -NH-CH-CH₂-C₆H₄Cl / CH₃ | 167-168 (MeoH-ether) | C₁₉H₂₈ClNOS. HCl | 59.05 | 58.90 | 6.50 | 6.50 | 3.60 | 3.60 |
| 53 | CH₃S- | 3CH₃ | -NH-(CH₂)₃-C₆H₅ | 180-182 (MeoH-ether) | C₁₉H₂₅NOS. HCl | 64.85 | 64.95 | 7.45 | 7.40 | 4.00 | 4.05 |
| 54 | CH₃S- | 3CH₃ | -NH-CH₂-C₆H₅ | 204-205 (MeoH-ether) | C₁₇H₂₁NOS. HCl | 63.00 | 62.95 | 6.80 | 6.60 | 4.30 | 4.25 |
| 55 | CH₃S- | 3CH₃ | -NH-(CH₂)₂-CH₃ | 130-131 (C₆H₆-CHCl₃) | C₁₃H₂₁NOS. HCl | 56.60 | 56.30 | 8.10 | 8.05 | 5.10 | 5.05 |
| 56 | CH₃S- | 3CH₃ | -NH-(CH₂)₇-CH₃ | 207.5-208.5 (MeoH-ether) | C₁₈H₃₁NOS. HCl | 62.50 | 62.40 | 9.30 | 9.40 | 4.05 | 4.05 |
| 57 | CH₃S- | 3CH₃ | -NH-(CH₂)₂-C₆H₅ | 153-154 (MeoH-ether) | C₁₈H₂₃NOS. HCl | 64.00 | 64.10 | 7.15 | 7.10 | 4.15 | 4.05 |
| 58 | CH₃S- | 3CH₃ | -NHsecC₄H₉ | 123-124 (MeoH-ether) | C₁₄H₂₃NOS. HCl | 58.00 | 57.90 | 8.20 | 8.20 | 4.65 | 4.55 |
| 59 | CH₃S- | 3C₂H₅ | -NHisoC₃H₇ | 109-110 (MeoH-ether) | C₁₄H₂₃NOS. HCl | 58.05 | 58.05 | 8.35 | 8.40 | 4.80 | 4.75 |
| 60 | CH₃S- | 3C₂H₅ | -NHsecC₄H₉ | 108-109 (MeoH-ether) | C₁₅H₂₅NOS. HCl | 59.30 | 59.15 | 8.60 | 8.65 | 4.60 | 4.50 |
| 61 | CH₃S- | 3C₂H₅ | -NH-C(CH₃)₃ | 112-113 (MeoH-ether) | C₁₅H₂₅NOS. HCl | 59.30 | 59.30 | 8.60 | 8.55 | 4.40 | 4.50 |
| 62 | CH₃S- | 3C₂H₅ | -NH-(CH₂)₇-CH₃ | 140-141 (MeoH-ether) | C₁₉H₃₃NOS. HCl | 63.40 | 63.20 | 9.50 | 9.60 | 3.90 | 4.05 |
| 63 | CH₃S- | 3F | -NHisoC₃H₇ | 124-125 (MeoH-ether) | C₁₂H₁₈FNOS. HCl | 51.50 | 51.25 | 6.85 | 6.85 | 5.00 | 5.00 |
| 64 | CH₃S- | 3F | -NH-(CH₂)₃CH₃ | 159-160 (MeoH-ether) | C₁₃H₂₀FNOS. HCl | 53.10 | 53.10 | 7.20 | 7.30 | 4.75 | 4.85 |
| 65 | CH₃S- | 3F | -NH-secC₄H₉ | 109-110 (MeoH-ether) | C₁₃H₂₀FNOS. HCl | 53.10 | 52.85 | 7.20 | 7.05 | 4.75 | 4.85 |
| 66 | CH₃S- | 3F | -NH-C(CH₃)₃ | 204-206 (MeoH-ether) | C₁₃H₂₀FNOS. HCl | 53.10 | 52.95 | 7.20 | 7.05 | 4.75 | 4.60 |
| 67 | CH₃S- | 3F | -NH-(CH₂)₇-CH₃ | 236-238 (MeoH-ether) | C₁₇H₂₈FNOS. HCl | 58.35 | 58.05 | 8.35 | 8.40 | 5.00 | 4.85 |
| 68 | iso-C₃H₇S- | 2CH₃ | -NHisoC₃H₇ | 140 (MeoH-ether) | C₁₅H₂₅NOS. HCl | 59.05 | 59.30 | 8.45 | 8.55 | 4.40 | 4.50 |
| 69 | iso-C₃H₇S- | 2CH₃ | -NH-C(CH₃)₃ | 205-207 (MeoH-ether) | C₁₆H₂₇NOS. HCl | 60.40 | 60.10 | 8.90 | 8.80 | 4.40 | 4.30 |
| 70 | CH₃S- | 2CH₃ | -NH-C(CH₃)₃ | 210-212 (MeoH-ether) | C₁₄H₂₃NOS. HCl | 58.00 | 57.85 | 8.35 | 8.40 | 4.80 | 4.60 |
| 71 | CH₃S- | 2CH₃ | -NH-(CH₂)₇-CH₃ | 189-190 (MeoH-ether) | C₁₈H₃₁NOS. HCl | 62.50 | 62.50 | 9.30 | 9.20 | 4.05 | 3.95 |
| 72 | CH₃S- | H | -NH-(CH₂)₇-CH₃ | 187-188 (MeoH-ether) | C₁₇H₂₉NOS. HCl | 61.50 | 61.30 | 9.10 | 9.15 | 4.20 | 4.10 |
| 73 | n-C₄H₉S- | 3CH₃ | -N(piperidino) | 210-214 (MeoH-ether) | C₂₁H₃₅NOS. HCl x | 65.68 | 65.85 | 8.92 | 8.90 | 3.65 | 3.55 |
| 74 | CH₃S- | 3CH₃ | -N(imidazolyl) | 138-139 (isoPrOH- | C₁₃H₁₆N₂OS x | 62.87 | 62.80 | 6.49 | 6.50 | 11.28 | 10.95 |

TABLE I-continued

Structure: R1, R2, R3 on phenyl ring; –CHOH–CH(R4)–N(R5)(R6)

R₃=R₄=H

| No | R₁ | R₂ | -N(R₅)(R₆) | M.P., °C (1) | Formula | C,% Calc. | C,% Found | H,% Calc. | H,% Found | N,% Calc. | N,% Found |
|---|---|---|---|---|---|---|---|---|---|---|---|
| | | | | (ether) | | | | | | | |
| 75 | CH₃S- | 2Cl | -N(piperidine) | 218-219 (acetone) | $C_{14}H_{20}ClNOS \cdot HCl$ x | 52.17 | 52.30 | 6.57 | 6.70 | 4.35 | 4.15 |
| 76 | CH₃S- | 3CH₃ | -N(piperidine)-pyridyl-CH₃ | 238-240 (MeOH) | $C_{21}H_{28}NOS \cdot 2HCl$ x | 64.20 | 64.05 | 7.45 | 7.35 | 7.10 | 6.90 |
| 77 | CH₃S- | 3CH₃ | -N(piperidine)-phenyl | 219-220 (MeOH-ether) | $C_{21}H_{29}NOS \cdot HCl$ x | 67.08 | 67.05 | 6.97 | 6.95 | 3.72 | 3.75 |
| 78 | CH₃S- | 3CH₃ | -N(piperidine)-C₂H₅ | 143-144 (acetone) | $C_{17}H_{27}NOS \cdot HCl$ x | 61.91 | 61.95 | 8.55 | 8.60 | 4.24 | 4.14 |
| 79 | n-C₄H₉S- | H | -NHisoC₃H₇ | 97,5-98,5 (MeOH-ether) | $C_{13}H_{23}NOS \cdot HCl$ | 59.28 | 59.02 | 8.62 | 8.55 | 4.61 | 4.88 |
| 80 | CH₃S- | 3CH₃ | -N(piperidine)-OH | 141-142 (acetone) | $C_{15}H_{23}NO_2S \cdot HCl$ x | 56.65 | 56.45 | 7.60 | 7.60 | 4.40 | 4.30 |
| 81 | CH₃S- | 3CH₃ | -N(piperidine)-(CH₂)₃-phenyl | 198-199 (acetone) | $C_{24}H_{33}NOS \cdot HCl$ x | 68.62 | 68.40 | 8.15 | 8.05 | 3.33 | 3.20 |
| 82 | n-C₄H₉S- | 3CH₃ | -N(piperidine) | 138-140 (acetone) | $C_{18}H_{29}NOS \cdot HCl$ x | 63.22 | 62.93 | 8.25 | 8.15 | 4.09 | 4.00 |
| 83 | n-C₄H₉S- | 3CH₃ | -N(piperidine)-CH₃ | 180-182 (acetone) | $C_{19}H_{31}NOS \cdot HCl$ x | 63.75 | 63.65 | 9.01 | 9.10 | 3.91 | 3.80 |
| 84 | iso-C₄H₉S- | 3CH₃ | -N(piperidine) | 165-167 (acetone) | $C_{18}H_{29}NOS \cdot HCl$ x | 62.85 | 62.25 | 8.79 | 8.90 | 4.07 | 3.80 |
| 85 | n-C₅H₁₁S- | 3CH₃ | -N(piperidine) | 150-152 (acetone) | $C_{19}H_{31}NOS \cdot HCl$ x | 63.75 | 63.72 | 9.01 | 9.20 | 3.91 | 3.65 |
| 86 | n-C₅H₁₁S | 3CH₃ | -N(piperidine)-CH₃ | 182-184 (acetone) | $C_{20}H_{33}NOS \cdot HCl$ x | 64.75 | 64.85 | 8.96 | 9.25 | 3.77 | 3.68 |
| 87 | n-C₈H₁₇S- | 3CH₃ | -N(piperidine)-CH₃ | 189-192 (MeOH-ether) | $C_{23}H_{39}NOS \cdot HCl$ x | 66.71 | 66.88 | 9.71 | 9.90 | 3.38 | 3.35 |
| 88 | n-C₈H₁₇S- | 3CH₃ | -N(piperidine) | 144,5-145,5 (MeOH-ether) | $C_{22}H_{37}NOS \cdot HCl$ x | 66.05 | 66.05 | 9.57 | 9.75 | 3.50 | 3.30 |
| 89 | n-C₁₀H₂₁S- | 3CH₃ | -N(piperidine) | 141,5-153,5 (MeOH-ether) | $C_{24}H_{41}NOS \cdot HCl$ x | 67.33 | 67.25 | 9.89 | 9.90 | 3.27 | 3.05 |
| 90 | nC₁₀H₂₁S- | 3CH₃ | -N(piperidine)-CH₃ | 196-200 (acetone) | $C_{25}H_{43}NOS \cdot HCl$ x | 67.91 | 67.80 | 10.03 | 9.90 | 3.17 | 3.95 |
| 91 | CH₃S- | 3Cl | -N(piperidine)-CH₃ | 250-252,5 (MeOH-ether) | $C_{15}H_{22}ClNOS \cdot HCl$ | 53.74 | 53.55 | 6.89 | 6.85 | 4.16 | 3.98 |
| 92 | CH₃S- | 2Cl | -N(piperidine)-CH₃ | 184-186,5 (MeOH-ether) | $C_{15}H_{22}ClNOS \cdot HCl$ x | 53.57 | 53.75 | 6.89 | 6.90 | 4.16 | 4.20 |

TABLE I-continued

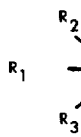

R₃=R₄=H

| No | R₁ | R₂ | -NR₅R₆ | M.P., °C⁽¹⁾ | Formula | C % Calc. | C % Found | H % Calc. | H % Found | N % Calc. | N % Found |
|----|-----|-----|--------|-------------|---------|-----------|-----------|-----------|-----------|-----------|-----------|
| 93 | CH₃SO₂ | 3CH₃ | -N(piperidine) | 204-205 (MeOH-ether) | C₁₅H₂₃NO₃S HCl x | 53.96 | 53.86 | 7.25 | 7.20 | 4.20 | 4.25 |
| 94 | CH₃S- | 3CH₃ | -N(4-methylpiperidine-CH₃) | 192-193 (MeOH-ether) | C₂₁H₂₈NOS HCl x | 64.20 | 63.85 | 7.45 | 7.50 | 7.10 | 7.05 |
| 95 | CH₃S- | 3CH₃ | -N(C₆H₁₁)₂ | 212-213 (isoPrOH) | C₂₂H₃₅NOS HCl x | 66.38 | 66.35 | 9.12 | 9.85 | 3.52 | 3.40 |
| 96 | n-C₄H₉S- | 3CH₃ | -N(C₆H₁₁)₂ | 163-164 (C₆H₆-ether de p.) | C₂₅H₄₁NOS HCl x | 68.22 | 68.40 | 9.62 | 9.55 | 3.18 | 2.95 |
| 97 | n-C₄H₉S- | 3CH₃ | -N(nC₃H₇)₂ | 144-145 (acetone-ether of p.) | C₁₉H₃₃NOS HCl x | 63.39 | 63.21 | 9.52 | 9.62 | 3.89 | 3.67 |
| 98 | CH₃S- | 3CH₃ | -NH-CH-CH(CH₃)₂ / CH₃ | 177 (MeOH-ether) | C₁₅H₂₅NOS HCl | 59.30 | 59.00 | 8.60 | 8.45 | 4.60 | 4.45 |
| 99 | iso C₃H₇S- | 3CH₃ | -N(piperidine)-CH₃ | 210-211 (MeOH-ether) | C₁₆H₂₉NOS HCl x | 62.85 | 62.90 | 8.80 | 8.85 | 4.05 | 3.80 |
| 100 | CH₃S- | 3F | -N(piperidine) | 194 (MeOH-ether) | C₁₄H₂₀FNOS HCl x | 55.50 | 55.40 | 6.90 | 6.95 | 4.60 | 4.55 |
| 101 | CH₃S- | 3C₂H₅ | -N(piperidine) | 205-206 (MeOH-ether) | C₁₆H₂₅NOS HCl x | 60.80 | 60.65 | 8.30 | 8.30 | 4.40 | 4.40 |
| 102 | CH₃S- | 3C₂H₅ | -N(piperidine)-CH₃ | 215-217 (MeOH-ether) | C₁₇H₂₇NOS HCl x | 61.90 | 62.05 | 8.55 | 8.45 | 4.20 | 4.05 |
| 103 | CH₃S- | 2CH₃ | -N(piperidine)-CH₃ | 228-229 (MeOH-ether) | C₁₆H₂₅NOS HCl x | 60.80 | 60.55 | 8.30 | 8.35 | 4.40 | .20 |
| 104 | CH₃S- | 3CH₃ | -NH-(cyclohexyl) | 183-184 (MeOH-ether) | C₁₆H₂₅NOS HCl | 60.80 | 60.70 | 8.30 | 8.15 | 4.25 | 4.25 |
| 105 | CH₃S- | 3CH₃ | -N(piperidine)-CH₃ | 234-235 (MeOH-ether) | C₁₆H₂₅NOS HCl x | 60.80 | 60.50 | 8.30 | 8.30 | 4.40 | 4.20 |
| 106 | CH₃S- | 3CH₃ | -N(piperidine-2-CH₃) | 198-199 (MeOH-ether) | C₁₆H₂₅NOS HCl x | 60.80 | 60.70 | 8.30 | 8.15 | 4.40 | 4.25 |
| 107 | C₂H₅S- | 3CH₃ | -N(piperidine)-CH₃ | 223,5-224,5 (MeOH-ether) | C₁₇H₂₇NOS HCl x | 61.90 | 61.60 | 8.55 | 8.45 | 4.25 | 4.00 |
| 108 | n-C₃H₇S- | 3CH₃ | -N(piperidine) | 160-161 (MeOH-ether) | C₁₇H₂₇NOS HCl x | 61.90 | 61.55 | 8.55 | 8.30 | 4.25 | 4.05 |
| 109 | CH₃S- | 3CH₃ | -N(tetrahydroisoquinoline) | 228-230 (isoPrOH-ether) | C₁₉H₂₃NOS HCl x | 65.22 | 65.10 | 6.92 | 6.85 | 4.00 | 3.95 |
| 110 | CH₃S- | 3CH₃ | -N(pyrrolidine) | 173-174 (isoPrOH) | C₁₄H₂₁NOS HCl x | 58.42 | 58.35 | 7.70 | 7.80 | 4.87 | 4.65 |
| 111 | CH-SO₂ | 3CH₃ | -NH-(CH₂)₃-CH₃ | 138-139 (acetone) | C₁₅H₂₅NO₃S HCl | 52.21 | 52.45 | 7.52 | 7.50 | 4.35 | 4.25 |

TABLE I-continued

$R_3 = R_4 = H$

| No | $R_1$ | $R_2$ | $-N\begin{matrix}R_5\\R_6\end{matrix}$ | M.P., °C[1] | Formula | C, % Calc. | C, % Found | H, % Calc. | H, % Found | N, % Calc. | N, % Found |
|---|---|---|---|---|---|---|---|---|---|---|---|
| 112 | $CH_3SO_2$ | $3CH_3$ | $-NHsec-C_4H_9$ | 164.5-165.5 (isoPrOH) | $C_{14}H_{25}NO_3S.HCl$ | 52.24 | 51.95 | 7.52 | 7.60 | 4.35 | 4.05 |
| 113 | $CH_3SO_2$ | $3CH_3$ | $-NH-CH-CH_2-\text{Ph}$ <br> $\quad\quad\;\;CH_3$ | 210-212 (isoPrOH) | $C_{19}H_{25}NO_3S.HCl$ | 59.44 | 59.60 | 6.83 | 6.70 | 3.65 | 3.35 |
| 114 | $CH_3SO_2$ | $3CH_3$ | $-NH-C_6H_{11}$ | 197.5-199 (MeoH-ether) | $C_{16}H_{25}NO_3S.HCl$ | 55.40 | 55.35 | 7.26 | 7.12 | 4.05 | 3.98 |
| 115 | $CH_3SO_2$ | $3CH_3$ | $-N\text{(piperidine)}-CH_3$ | 253-254 | $C_{16}H_{25}NO_3S.$ (MeoH-ether) HCl x | 54.50 | 54.29 | 7.60 | 7.63 | 3.65 | 3.47 |
| 116 | $CH_3SO_2$ | $3CH_3$ | $-N\text{(piperazine)}N-CH_3$ | 149-250 (MeoH-ether) | $C_{15}H_{24}N_2O_3S.2HCl$ x | 45.70 | 45.92 | 6.65 | 6.73 | 6.85 | 6.72 |
| 117 | $CH_3S-$ | $3COOH$ | $-N\text{(piperidine)}$ | 251-252 ($H_2O$) | $C_{15}H_{21}NO_3S.HCl$ x | 60.99 | 60.82 | 7.17 | 7.02 | 4.74 | 4.50 |
| 118 | $C_2H_5S-$ | $3NO_2$ | $-N\text{(piperidine)}$ | 151-152 (MeoH-ether) | $C_{13}H_{22}N_2O_3S.HCl$ x | 51.94 | 52.03 | 6.68 | 6.51 | 8.06 | 8.12 |
| 119 | $C_2H_5S-$ | $3NO_2$ | $-NH-isoC_3H_7$ | 121-123 (MeoH-ether) | $C_{13}H_{20}N_2O_3S.HCl$ | 48.67 | 48.83 | 6.60 | 6.48 | 8.73 | 8.88 |
| 120 | $CH_3S-$ | $CH_3S$ | $-NHisoC_3H_7$ | 173-175 (MeoH-ether) | $C_{13}H_{21}NOS_2.HCl$ | 50.71 | 50.79 | 7.20 | 6.99 | 4.55 | 4.48 |
| 121 | $CH_3S-$ | $3CH_3S$ | $-NH-C(CH_3)_3$ | 153-155 (MeoH-ether) | $C_{14}H_{23}NOS_2.HCl$ | 48.38 | 48.50 | 8.12 | 8.16 | 4.70 | 4.72 |
| 122 | $CH_3S-$ | $3CH_3$ | $-NH-(CH_2)_3-C_6H_{11}$ | 225-226 (MeoH-ether) | $C_{19}H_{30}N_2OS.2HCl$ | 60.23 | 60.22 | 8.70 | 8.68 | 7.80 | 7.93 |
| 123 | $CH_3S$ | $3NH-COCH_3$ | $-NHisoC_3H_7$ | 193-194 (acetone) | $C_{14}H_{22}N_2O_2S.HCl$ | 52.73 | 52.88 | 7.27 | 7.17 | 8.79 | 8.91 |
| 124 | $CH_3SO$ | $3CH_3$ | $-NHisoC_3H_7$ | 111-113 ($CHCl_3$-ether) | $C_{13}H_{21}NO_4S.HCl$ | 61.14 | 60.92 | 8.29 | 8.13 | 5.48 | 5.35 |
| 125 | $CH_3S-$ | $3CH_3$ | $-N\text{(piperazine)}N-CH_2-\text{Ph}$ | 154 (isoPrOH) | $C_{21}H_{28}N_2OS.$ x | 70.75 | 70.55 | 7.90 | 7.90 | 7.85 | 7.70 |
| 126 | $CH_3S-$ | $3CH_3$ | $-N\text{(piperazine)}N-\text{Py-Cl}$ | 168-168.5 (MeoH-ether) | $C_{20}H_{25}ClN_2OS.2HCl$ x | 53.40 | 53.15 | 6.05 | 6.05 | 6.20 | 6.00 |
| 127 | $CH_3COS-$ | $H$ | $-NHisoC_3H_7$ | 142-144 (MeoH-ether) | $C_{13}H_{19}NO_2S.HCl$ | 53.87 | 53.69 | 6.96 | 6.88 | 4.83 | 4.72 |
| 128 | $CH_3COS-$ | $3CH_3$ | $-NHisoC_3H_7$ | 182-183 (MeoH-ether) | $C_{14}H_{21}NO_2S.2HCl$ | 55.34 | 55.28 | 7.30 | 7.32 | 4.61 | 4.48 |
| 129 | $CH_3S-$ | $3NH_2$ | $-NHisoC_3H_7$ | 212-213 (isoPrOH-ether) | $C_{12}H_{20}N_2OS.2HCl$ | 46.00 | 45.88 | 7.08 | 7.12 | 8.94 | 8.83 |
| 130 | $CH_3S-$ | $3CH_3O$ | $-N\text{(piperidine)}$ | 198.200 (MeoH-ether) | $C_{15}H_{23}NO_2S.HCl$ x | 56.65 | 56.35 | 7.60 | 7.60 | 4.40 | 4.15 |
| 131 | $CH_3S-$ | $3Cl$ | $-NH-C_7H_{13}$ | 172-173 (MeoH-ether) | $C_{17}H_{26}ClNOS.HCl$ | 56.04 | 55.91 | 7.17 | 7.32 | 3.84 | 3.91 |
| 132 | $-SH$ | $H$ | $-NHisoC_3H_7$ | 176-177 (isoPrOH-ether) | $C_{11}H_{18}NOS_2.HCl$ | 53.32 | 52.88 | 7.32 | 7.52 | 5.65 | 5.75 |
| 133 | $-SH$ | $3CH_3$ | $-NH-t(CH_3)_3$ | 181-182 (MeoH-ether) | $C_{13}H_{22}NOS_2.HCl$ | 56.61 | 56.33 | 8.04 | 8.21 | 5.08 | 5.33 |
| 134 | $iso-C_3H_7SO_2$ | $3CH_3$ | $-N\text{(piperidine)}$ | 191-192 (MeoH-ether) | $C_{17}H_{27}NO_3S.HCl$ x | 56.40 | 56.55 | 7.80 | 7.90 | 3.85 | 4.00 |
| 135 | $CH_3S-$ | $3CH_3$ | $-N\text{(piperazine)}N-\text{Ph-OCH}_3$ | 165-166 | $C_{21}H_{28}N_2OS.$ | 61.65 | 61.55 | 7.15 | 7.10 | 6.85 | 6.49 |

3,954,871

TABLE I-continued

R₃=R₄=H

| No | R₁ | R₂ | -N(R₅)(R₆) | M.P., °C | Formula | C % Calc. | C % Found | H % Calc. | H % Found | N % Calc. | N % Found |
|----|----|----|-----------|----------|---------|-----------|-----------|-----------|-----------|-----------|-----------|
|    |    |    |           | (MeoH-ether) | HCl x |       |       |       |       |       |       |
| 136 | iso-C₃H₇S- | 3CH₃ | -NH-CH₂-C₆H₅ | 179-180 (MeoH-ether) | C₁₉H₂₅NOS. HCl | 64.85 | 64.45 | 7.45 | 7.45 | 4.00 | 3.85 |
| 137 | n-C₄H₉S- | 3CH₃ | -NH-(CH₂)₃-CH₃ | 202-204.5 (MeoH-ether) | C₁₇H₂₉NOS. HCl | 61.51 | 61.66 | 9.11 | 9.17 | 4.22 | 4.18 |
| 138 | CH₃S- | 3Cl | -NH-secC₄H₉ | 74-75(C₆H₁₂) | C₁₃H₂₀ClNOS. | 57.02 | 56.97 | 7.36 | 7.32 | 5.11 | 4.92 |
| 139 | CH₃S- | 3Cl | -NH-(CH₂)₂-CH₃ | 175-177 (MeoH-ether) | C₁₂H₁₈ClNOS. HCl | 48.65 | 49.07 | 6.47 | 6.58 | 4.73 | 4.56 |
| 140 | n-C₄H₉S- | 3CH₃ | -NH-C(CH₃)₃ | 119-120 (MeoH-ether) | C₁₇H₂₉NOS. HCl | 61.51 | 61.45 | 9.11 | 9.05 | 4.22 | 4.16 |
| 141 | n-C₄H₉S- | 3CH₃ | -NHisoC₃H₇ | 113.5-115.5 (MeoH-ether) | C₁₇H₂₉NOS. HCl | 62.86 | 62.74 | 8.79 | 9.07 | 4.07 | 3.95 |
| 142 | n-C₆H₁₃S- | 3CH₃ | -NH-C(CH₃)₃ | 129-132 (MeoH-ether) | C₁₇H₃₁NOS. HCl | 63.75 | 63.38 | 9.01 | 9.23 | 3.91 | 3.85 |
| 143 | CH₃S- | 3Cl | -NH-C(CH₃)₃ | 224.5-225.5 (MeoH-ether) | C₁₄H₂₃NOS. HCl | 50.32 | 50.18 | 6.82 | 6.72 | 4.51 | 4.40 |
| 144 | CH₃S- | 3Cl | -NH-(CH₂)₃-CH₃ | 195-197.5 (MeoH-ether) | C₁₃H₂₀ClNOS. HCl | 50.32 | 50.36 | 6.82 | 6.76 | 4.52 | 4.40 |
| 145 | n-C₄H₉S- | 3CH₃ | -NHisoC₃H₇ | 125.5-127 (MeoH-ether) | C₁₆H₂₇NOS. HCl | 60.45 | 60.59 | 8.88 | 8.94 | 4.40 | 4.30 |
| 146 | CH₃S- | 3Cl | -NH-CH(CH₃)-CH₂-C₆H₅ | 139-141.5 (isoProH) | C₁₈H₂₂ClNOS. HCl | 58.06 | 57.92 | 6.23 | 6.18 | 3.76 | 3.75 |
| 147 | n-C₄H₉S- | 3CH₃ | -NH-C₆H₁₁ | 111-112.5 (Ac-Eth) | C₁₃H₂₉NOS. HCl | 62.85 | 62.90 | 8.79 | 8.68 | 4.07 | 3.98 |
| 148 | n-C₄H₉S- | 3CH₃ | -N(piperidinyl-CH₃) | 156-157 (MeoH-ether) | x C₁₉H₂₈NOS. HCl | 63.75 | 63.36 | 9.01 | 8.96 | 3.91 | 3.78 |
| 149 | n-C₄H₉S- | 3CH₃ | -N(piperidinyl-CH₃) | 184-186 (MeoH-ether) | x C₁₉H₂₈NOS. HCl | 63.75 | 63.63 | 9.01 | 9.04 | 3.91 | 3.56 |
| 150 | CH₃S- | 3Cl | -N(CH₃)₂ | 180.5-182.5 (MeoH-ether) | x C₁₁H₁₆ClNOS. HCl | 46.81 | 47.02 | 6.07 | 6.14 | 4.96 | 4.96 |
| 151 | n-C₄H₉S- | 3CH₃ | -N(CH₃)₂ | 108-109 (MeoH-ether) | x C₁₅H₂₅NOS. HCl | 59.29 | 59.20 | 8.62 | 8.96 | 4.61 | 4.54 |
| 152 | CH₃S- | 3Cl | -N(morpholinyl) | 172-174 (MeoH-ether) | x C₁₃H₁₈ClNO₂S. HCl | 48.15 | 48.10 | 5.91 | 5.92 | 4.32 | 4.25 |
| 153 | CH₃S- | 3Cl | -N(piperidinyl) | 226.5-228.5 (MeoH-ether) | x C₁₄H₂₀ClNOS. HCl | 52.17 | 52.20 | 6.57 | 6.62 | 4.35 | 4.34 |
| 154 | CH₃S- | 3CH₃ | -NH-C(CH₃)₃ | 220-222 (MeoH-ether) | C₁₄H₂₃NOS. HCl | 58.00 | 58.00 | 8.35 | 8.40 | 4.80 | 4.80 |
| 155 | CH₃S- | 3CH₃ | -N(piperidinyl) | 197-198 (MeoH-ether) | x C₁₅H₂₂NOS. HCl | 59.70 | 60.10 | 8.00 | 8.25 | 4.60 | 4.35 |
| 156 | C₂H₅S- | 3CH₃ | -NHisoC₃H₇ | 128-129 (MeoH-ether) | C₁₄H₂₃NOS. HCl | 58.00 | 58.30 | 8.35 | 8.10 | 4.80 | 4.60 |
| 157 | C₂H₅S- | 3CH₃ | -N(piperidinyl) | 192.5-193.5 (MeoH-ether) | x C₁₆H₂₅NOS. HCl | 60.80 | 60.60 | 8.30 | 8.25 | 4.40 | 4.05 |
| 158 | iso-C₃H₇S- | 3CH₃ | -NHisoC₃H₇ | 133-134 (EtOH-ether) | C₁₅H₂₄NOS. HCl | 59.30 | 59.00 | 8.60 | 8.70 | 4.60 | 4.70 |
| 159 | iso-C₃H₇S- | 3CH₃ | -NH-C(CH₃)₃ | 182-183 (MeoH-ether) | C₁₆H₂₆NOS. HCl | 60.45 | 60.50 | 8.90 | 8.80 | 4.40 | 4.30 |
| 160 | iso-C₃H₇S- | 3CH₃ | -N(piperidinyl) | 177-179 (MeoH-ether) | x C₁₇H₂₇NOS. HCl | 61.80 | 61.50 | 8.55 | 8.60 | 4.25 | 4.15 |

TABLE I-continued

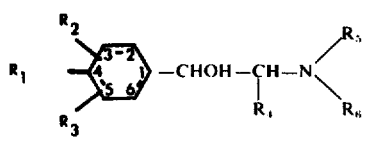

$R_3=R_4=H$

| No | $R_1$ | $R_2$ | $-N\begin{subarray}{l}R_5\\R_6\end{subarray}$ | M.P., °C(1) | Formula | C, % Calc. | C, % Found | H, % Calc. | H, % Found | N, % Calc. | N, % Found |
|---|---|---|---|---|---|---|---|---|---|---|---|
| 161 | iso-$C_3H_7S$- | 3$CH_3$ | -N○O | 192-193 (MeoH-ether) | x $C_{16}H_{25}NO_2S$. HCl | 57.90 | 57.60 | 7.90 | 7.90 | 4.20 | 4.10 |
| 162 | n-$C_6H_{13}S$- | 3$CH_3$ | -N○O | 157.5-159 (isoProH-ether) | x $C_{19}H_{31}NO_2S$. HCl | 61.34 | 61.79 | 8.13 | 8.22 | 3.76 | 4.48 |
| 163 | n-$C_6H_{13}S$- | 3$CH_3$ | -N○ | 146-147 (MeoH-ether) | x $C_{20}H_{33}NOS$. HCl | 64.92 | 65.25 | 8.72 | 9.01 | 3.78 | 3.40 |
| 164 | iso-$C_3H_7S$- | 3$CH_3$ | -NH-$CH_2$-$CH_2$-○ | 168-169 (MeoH-ether) | $C_{20}H_{27}NOS$. HCl | 65.65 | 65.60 | 7.70 | 7.55 | 3.80 | 3.70 |
| 165 | $CH_3S$- | 3$CH_3$ | -NH-⟨H⟩ | 127-130 (MeoH-ether) | $C_{15}H_{23}NOS$. HCl | 59.70 | 59.90 | 8.00 | 8.20 | 4.70 | 4.50 |
| 166 | $C_2H_5S$- | 3$CH_3$ | -NHsec$C_4H_9$ | 99-101 (MeoH-ether) | $C_{15}H_{25}NOS$. HCl | 59.30 | 59.10 | 8.60 | 8.50 | 4.60 | 4.40 |
| 167 | $C_2H_5S$- | 3$CH_3$ | -N○O | 157-159 (MeoH-ether) | x $C_{15}H_{23}NO_2S$. HCl | 56.70 | 57.00 | 7.60 | 7.70 | 4.40 | 4.58 |
| 168 | $C_2H_5S$- | 3$CH_3$ | -NH-⟨H⟩ | 153-156 (MeoH-ether) | $C_{17}H_{27}NOS$. HCl | 61.90 | 61.62 | 8.55 | 8.40 | 4.25 | 4.10 |
| 169 | $CH_3S$- | 3$CH_3$ | -NH-$(CH_2)_3CH_3$ | 180-182 (MeoH-ether) | $C_{14}H_{23}NOS$. HCl | 58.00 | 57.90 | 8.35 | 8.20 | 4.90 | 4.75 |

(1) The recrystallisation solvent is given between brackets

TABLE II

| No | $R_1$ | $R_2$ | $R_3$ | $R_4$ | $-N\begin{subarray}{l}R_5\\R_6\end{subarray}$ | M.P., °C | Formula | C, % Calc. | C, % Found | H, % Calc. | H, % Found | N, % Calc. | N, % Found |
|---|---|---|---|---|---|---|---|---|---|---|---|---|---|
| 1 | $CH_3S$- | 3Cl | 5$CH_3$ | H | -NHsec$C_4H_9$ | 134-136 (MeoH-ether) | $C_{14}H_{22}ClNOS$.HCl | 51.85 | 51.85 | 7.15 | 7.25 | 4.32 | 4.20 |
| 2 | $CH_3S$- | 3Cl | 5$CH_3$ | H | -NHiso$C_3H_7$ | 137.5-140 (MeoH-ether) | $C_{13}H_{20}ClNOS$.HCl | 50.32 | 50.40 | 6.82 | 6.90 | 4.51 | 4.45 |
| 3 | $CH_3S$- | 3Cl | 5$CH_3$ | H | -NH-C$(CH_3)_3$ | 244.5-246.5 (MeoH-ether) | $C_{14}H_{22}ClNOS$.HCl | 51.85 | 51.65 | 7.15 | 7.20 | 4.32 | 4.25 |
| 4 | $CH_3S$- | 3Cl | 5$CH_3$ | H | -NH-$(CH_2)_7$-$CH_3$ | 185-188 (acetone) | $C_{18}H_{30}ClNOS$.HCl | 56.83 | 56.75 | 8.21 | 8.30 | 8.68 | 8.60 |
| 5 | $CH_3S$- | 3Cl | H | n$C_3H_7$ | -NH-sec$C_4H_9$ | 193-194.5 (isoPrOH) | $C_{16}H_{26}ClNOS$.HCl | 54.54 | 54.51 | 7.72 | 7.76 | 3.98 | 3.83 |
| 6 | $CH_3S$- | 3$CH_3$ | H | $C_2H_5$ | -NHsec$C_4H_9$ | 197-200 (MeoH-ether) | $C_{16}H_{27}NOS$.HCl x | 60.45 | 60.20 | 8.88 | 8.80 | 4.41 | 4.25 |
| 7 | $CH_3S$- | 3$CH_3$ | H | $C_2H_5$ | -NH C$(CH_3)_3$ | 234-237 (MeoH-ether) | $C_{16}H_{27}NOS$.HCl | 60.45 | 60.25 | 8.88 | 8.80 | 4.41 | 4.15 |
| 8 | iso $C_3H_7S$- | 3$CH_3$ | H | $C_2H_5$ | -NH-$(CH_2)_7$-$CH_3$ | 174-175 (acetone) | $C_{22}H_{39}NOS$.HCl | 65.72 | 65.60 | 10.03 | 10.00 | 3.48 | 3.35 |
| 9 | iso $C_3H_7S$- | 3$CH_3$ | H | $CH_3$ | -NH-$(CH_2)_7$-$CH_3$ | 210-212 (isoPrOH) | $C_{19}H_{37}NOS$.HCl | 64.99 | 65.10 | 9.87 | 9.95 | 3.61 | 3.55 |
| 10 | $CH_3S$- | 3Cl | H | $C_2H_5$ | -N$(CH_3)_2$ | 229-232.5 (MeoH-ether) | $C_{13}H_{20}ClNOS$.HCl x | 50.32 | 50.12 | 6.82 | 6.70 | 4.51 | 4.43 |
| 11 | $CH_3S$- | 3Cl | H | $C_2H_5$ | -N○O | 189-191.5 (MeoH-ether) | $C_{15}H_{22}ClNOS$.HCl x | 51.14 | 50.94 | 6.58 | 6.48 | 3.98 | 3.98 |
| 12 | $CH_3S$- | 3Cl | H | $C_2H_5$ | -N○ | 217-219.5 (MeoH-ether) | $C_{16}H_{24}ClNOS$.HCl x | 54.85 | 54.65 | 7.19 | 7.00 | 4.00 | 3.92 |
| 13 | $CH_3S$- | 3Cl | H | $C_2H_5$ | -NH-$(CH_2)_7$ | 186.5-188.5 (acetone) | $C_{19}H_{32}ClNOS$.HCl | 57.86 | 57.69 | 8.43 | 8.50 | 3.55 | 3.40 |
| 14 | $CH_3S$- | 3Cl | 5$CH_3$ | H | -N○ | 163-166 (MeoH-ether) | $C_{15}H_{22}ClNOS$.HCl x | 53.57 | 53.71 | 6.89 | 7.05 | 4.16 | 4.00 |

TABLE II-continued

| No | $R_1$ | $R_2$ | $R_3$ | $R_4$ | $-N\!\!<\!\!^{R_5}_{R_6}$ | M.P., °C | Formula | C, % Calc. | C, % Found | H, % Calc. | H, % Found | N, % Calc. | N, % Found |
|---|---|---|---|---|---|---|---|---|---|---|---|---|---|
| 15 | $CH_3S-$ | 3Cl | H | $C_2H_5$ | $-NHisoC_3H_7$ | 241.5-243.5 (MeOH-ether) | $C_{14}H_{22}ClNOS.HCl$ | 51.85 | 52.00 | 7.15 | 7.07 | 4.32 | 4.10 |
| 16 | $CH_3S-$ | 3Cl | H | $C_2H_5$ | $-NH-C(CH_3)_3$ | 240.5-243 (MeOH-ether) | $C_{15}H_{24}ClNOS.HCl$ | 53.25 | 53.41 | 7.45 | 7.47 | 4.14 | 4.08 |
| 17 | $CH_3S-$ | $3CH_3$ | H | $CH_3$ | $-NH-C(CH_3)_3$ | 214-216 (MeOH-ether) | $C_{15}H_{25}NOS.HCl$ | 59.24 | 59.05 | 8.62 | 8.58 | 4.61 | 4.38 |
| 18 | $CH_3S-$ | $3CH_3$ | H | $CH_3$ | $-NHisoC_3H_7$ | 224-225 (MeOH-ether) | $C_{14}H_{23}NOS.HCl$ | 58.01 | 57.96 | 8.35 | 8.36 | 4.83 | 4.73 |
| 19 | $CH_3S-$ | $3CH_3$ | H | $CH_3$ | $-NHsecC_4H_9$ | 166-168 (MeOH-ether) | $C_{15}H_{25}NOS.HCl$ | 59.29 | 59.11 | 8.62 | 8.52 | 4.61 | 4.38 |
| 20 | $CH_3S-$ | $3CH_3$ | H | $CH_3$ | $-NH-(CH_2)_2-CH_3$ | 211-212 (MeOH-ether) | $C_{14}H_{23}NOS.HCl$ | 58.01 | 57.88 | 8.35 | 8.27 | 4.83 | 4.76 |
| 21 | $CH_3S-$ | 3Cl | H | $CH_3$ | $-NHisoC_3H_7$ | 260-262 (MeOH-ether) | $C_{13}H_{20}ClNOS.HCl$ | 50.32 | 50.35 | 6.82 | 6.75 | 4.51 | 4.42 |
| 22 | $CH_3S-$ | 3Cl | H | $CH_3$ | $-NH-C(CH_3)_3$ | 219-222 (MeOH-ether) | $C_{14}H_{22}ClNOS.HCl$ | 51.84 | 51.84 | 7.15 | 7.16 | 4.32 | 4.24 |
| 23 | $CH_3S-$ | 3Cl | H | $CH_3$ | $-NHsecC_4H_9$ | 189-190 (MeOH-ether) | $C_{14}H_{22}ClNOS.HCl$ | 51.84 | 51.84 | 7.15 | 7.08 | 4.32 | 4.17 |
| 24 | $CH_3S-$ | $3CH_3$ | H | $CH_3$ | $-N(CH_3)_2$ | 194-195 (MeOH-ether) | x $C_{13}H_{21}NOS.HCl$ | 56.60 | 56.46 | 8.04 | 8.05 | 5.08 | 5.12 |
| 25 | $CH_3S-$ | 3Cl | H | $C_2H_5$ | $-N(CH_3)_2$ | 229-232.5 (MeOH-ether) | x $C_{12}H_{18}ClNOS.HCl$ | 50.32 | 50.00 | 6.82 | 6.70 | 4.51 | 4.43 |
| 26 | $CH_3S-$ | 3Cl | H | $C_2H_5$ | -N(piperidinyl) | 216.5-220 (MeOH-ether) | x $C_{16}H_{24}ClNOS.HCl$ | 54.85 | 54.72 | 7.19 | 7.23 | 3.40 | 3.51 |
| 27 | $CH_3S-$ | $3CH_3$ | H | $CH_3$ | -N(morpholinyl) | 199-200 (MeOH-ether) | x $C_{15}H_{23}NO_2S.HCl$ | 56.68 | 56.42 | 7.60 | 7.45 | 4.40 | 4.23 |
| 28 | $CH_3S-$ | $3CH_3$ | H | $CH_3$ | -N(4-methylpiperidinyl) | 228-229 (MeOH-ether) | x $C_{17}H_{27}NOS.HCl$ | 61.98 | 61.75 | 8.56 | 8.55 | 4.25 | 4.25 |
| 29 | $CH_3S-$ | $3CH_3$ | H | $CH_3$ | -N(piperidinyl) | 227.5-230.5 (MeOH-ether) | x $C_{16}H_{25}NOS.HCl$ | 60.83 | 60.94 | 8.30 | 8.31 | 4.43 | 4.36 |

(1)The recrystallisation solvent is given between brackets

Hereinafter, pharmacological results are given for a lot of products according to the invention, as compared with known products. The $LD_{50}$ value was obtained by Campbell and Richter technique (Acta pharmacol. et toxicol. 1967, 25, 345).

TABLE III

| No. | $R_1$ | $R_2$ | $R_3$ | $R_4$ | $-N\!\!<\!\!^{R_5}_{R_6}$ | $LD_{50}$ intraperitoneal, mouse, mg/kg | Auricle of guinea pig[1] | Pipherical vasodilatator activity[2] |
|---|---|---|---|---|---|---|---|---|
| 1 | $CH_3S-$ | $3CH_3$ | H | H | $-NH-CH(CH_3)_2$ | 150 | ++ | +++ |
| 2 | $CH_3S-$ | 3Cl | H | H | $-NH-C(CH_3)_3$ | — | ++ | ++ |
| 3 | $CH_3S-$ | 3Cl | H | $CH_3$ | $-NH-C(CH_3)_3$ | 440 | ++ | +++ |
| 4 | $CH_3S-$ | $3CH_3$ | H | $CH_3$ | $-NH-CH(CH_3-NH-CH(CH_2$ | 300 | ++ | +++ |
| 5 | $CH_3S-$ | $3CH_3$ | H | $CH_3$ | $-NH-CH-CH_2-CH_3$ / $CH_3$ | 182 | + | ++++ |
| 6 | $CH_3S-$ | $3CH_3$ | H | $CH_3$ | $-NH-C(CH_3)_3$ | 220 | + | ++ |
| 7 | $CH_3S-$ | 3Cl | H | $CH_3$ | $-NH-CH(CH_3)_2$ | — | + | ++ |
| 8 | $CH_3S-$ | 3Cl | H | $CH_3$ | $-NH-CH-CH_2-CH_3$ / $CH_3$ | 150 | + | +++ |
| 9 | $CH_3S-$ | $3CH_3$ | H | $CH_3$ | $-NH-(CH_2)_3CH_3$ | 150 | ++ | +++ |
| 10 | $CH_3S-$ | 3Cl | H | H | $-NH-CH-CH_2-CH_3$ / $CH_3$ | 75 | ++ | +++ |
| 11 | $CH_3S-$ | 3Cl | H | H | $-NH-CH(CH_3)_2$ | 150 | ++ | +++ |
| 12 | $CH_3S-$ | $3CH_3$ | H | H | $-NH-C(CH_3)_3$ | 182 | + | ++++ |
| 13 | $CH_3S-$ | $3CH_3$ | H | H | -N(piperidinyl) | 364 | 0 | ++ |
| 14 | $CH_3S-$ | 3Cl | H | H | $-NH-(CH_2)_2-CH_3$ | 75 | ++ | +++ |
| 15 | $CH_3S-$ | 3Cl | H | H | $-NH-(CH_2)_3-CH_3$ | 110 | ++ | ++++ |
| 16 | $CH_3S-$ | 3Cl | H | $C_2H_5$ | $-NH-CH(CH_3)_2$ | — | 0 | ++ |
| 17 | $CH_3S-$ | 3Cl | H | $C_2H_5$ | $-NH-CH-CH_2CH_3$ / $CH_3$ | 364 | ++ | +++ |
| 18 | $CH_3S-$ | 3Cl | H | $C_2H_5$ | $-NH-C(CH_3)_3$ | 728 | 0 | ++ |
| 19 | $CH_3S-$ | $3CH_3$ | H | $CH_3$ | -N(morpholinyl) | — | 0 | ++ |

TABLE III-continued

| No. | R₁ | R₂ | R₃ | R₄ | -N⟨R₅/R₆ | LD₅₀ intraperitoneal, mouse, mg/kg | Auricle of guinea pig[1] | Peripherical vasodilatator activity[2] |
|---|---|---|---|---|---|---|---|---|
| 20 | CH₃S- | 3CH₃ | H | CH₃ | -N(piperidine)-CH₃ | 91 | 0 | ++++ |
| 21 | CH₃S- | 3CH₃ | H | CH₃ | -N(CH₃)₂ | 182 | ++ | +++ |
| 22 | CH₃S- | 3Cl | H | H | -NH-CH(CH₃)-CH₂-C₆H₅ | 55 | 0 | +++ |
| 23 | CH₃S- | 3Cl | H | H | -N(morpholine) | 728 | + | + |
| 24 | CH₃S- | 3Cl | H | H | -N(piperidine) | 364 | 0 | +++ |
| 25 | CH₃S- | 3CH₃ | H | CH₃ | -N(piperidine) | — | + | ++++ |
| 26 | CH₃S- | 3CH₃ | H | H | -N(morpholine) | 600 | 0 | +++ |
| 27 | CH₃S- | 3Cl | H | C₂H₅ | -N(CH₃)₂ | — | 0 | +++ |
| 28 | CH₃S- | 3Cl | H | C₂H₅ | -N(piperidine) | — | 0 | ++ |
| 29 | CH₃S- | 3CH₃ | H | H | -NH-(cyclopentyl) | 220 | ++ | ++++ |
| 30 | CH₃S- | 3CH₃ | H | H | NH-(CH₂)₃CH₃ | — | ++ | ++++ |
| 31 | CH₃S- | 3CH₃ | H | H | -NH-CH(CH₃)-CH₂-C₆H₅ | 75 | ++ | ++++ |
| 32 | CH₃S- | 3Cl | H | C₂H₅ | -NH(CH₂)₇-CH₃ | — | 0 | ++++ |
| 33 | CH₃S- | 3CH₃ | H | H | -NH-CH(CH₃)-CH₂-CH₃ | — | ++ | +++ |
| 34 | CH₃S- | 3CH₃ | H | H | -NH-(cyclohexyl) | — | ++ | ++++ |
| 35 | CH₃S- | 3CH₃ | H | H | -NH-(CH₂)₂-C₆H₅ | — | 0 | ++ |
| 36 | CH₃S- | 3CH₃ | H | C₂H₅ | -NH-CH(CH₃)₂ | — | 0 | +++ |
| 37 | CH₃S- | 3CH₃ | H | C₂H₅ | -NH-C(CH₃)₃ | — | 0 | +++ |
| 38 | CH₃S- | 3CH₃ | H | H | -NH(CH₂)₃-CH₃ | — | 0 | +++ |
| 39 | CH₃S- | 3CH₃ | H | C₂H₅ | -NH-CH(CH₃)-CH₂-CH₃ | — | 0 | +++ |
| 41 | CH₃S- | 3CH₃ | H | H | -NH₂ | 150 | 0 | 0 |
| 42 | CH₃S- | 3CH₃ | H | H | -N(piperidine)-CH₃ | 91 | + | +++ |
| 43 | CH₃S- | 3CH₃ | H | H | -NH-CH(CH₃)-CH₂-C₆H₃(Cl)₂ | 150 | + | ++++ |
| 44 | CH₃S- | 3CH₃ | H | H | -NH-CH(CH₃)-CH₂-C₆H₄Cl | 75 | + | ++++ |
| 45 | CH₃S- | 3C₂H₅ | H | H | -NH-(CH₂)₇-CH₃ | 75 | + | ++++ |
| 46 | CH₃S- | 3C₂H₅ | H | H | -N(piperidine) | — | ++ | +++ |

TABLE III-continued

| No. | R₁ | R₂ | R₃ | R₄ | $-N\begin{smallmatrix}R_5\\R_6\end{smallmatrix}$ | LD₅₀ intraperitoneal, mouse, mg/kg | Auricle of guinea pig⁽¹⁾ | Peripherical vasodilatator activity⁽²⁾ |
|---|---|---|---|---|---|---|---|---|
| 47 | CH₃S– | 3C₂H₅ | H | H | –NH–CH(CH₃)₂ | – | ++ | +++ |
| 48 | CH₃S– | 3C₂H₅ | H | H | –N(piperidinyl)–CH₃ | – | + | +++ |
| 49 | CH₃S– | 3CH₃ | H | H | –NH–CH(CH₃)–CH₂–C₆H₄–CH₃ | 91 | + | ++++ |
| 50 | CH₃S– | 3C₂H₅ | H | H | –NH–C(CH₃)₃ | 150 | ++ | +++ |
| 51 | CH₃S– | 3C₂H₅ | H | H | –NH–CH(CH₃)–CH₂–CH₃ | – | ++ | +++ |
| 52 | CH₃S– | 3Cl | H | H | –N(piperidinyl)–CH₃ | – | + | ++++ |
| 53 | CH₃S– | 3CH₃ | H | H | –NH–(CH₂)₃–C₆H₅ | – | + | ++++ |
| 54 | CH₃S– | 3CH₃ | H | H | –NH–(CH₂)₆–CH₃ | – | + | +++ |
| 55 | CH₃S– | 3CH₃ | H | H | –NH–(CH₂)₉–CH₃ | – | + | ++++ |
| 56 | CH₃S– | 3CH₃ | H | H | –NH–CH₂–C₆H₅ | – | + | ++ |
| 57 | CH₃S– | 3Cl | H | H | –NH–(CH₂)₃OCH₃ | – | ++ | + |
| 58 | CH₃S– | 3F | H | H | –NH–CH(CH₃)₂ | – | ++ | + |
| 59 | CH₃S– | 3Cl | H | H | –NH–(CH₂)₃OH | – | ++ | 0 |
| 60 | CH₃S– | 3CH₃ | H | H | –N(piperidinyl)–CH₂–C₆H₅ | – | ++ | ++ |
| 61 | CH₃S– | 2CH₃ | H | H | | – | + | +++ |
| 62 | CH₃S– | 3Cl | 5CH₃ | H | –N(piperidinyl) | 220 | + | ++ |
| 63 | CH₃S– | 3Cl | 5CH₃ | H | –NH–CH(CH₃)–CH₂–CH₃ | – | + | +++ |
| 64 | CH₃S– | 3Cl | 5CH₃ | H | –NH–CH(CH₃)₂ | 182 | ++ | +++ |
| 65 | CH₃S– | 3Cl | 5CH₃ | H | –NH–C(CH₃)₃ | – | 0 | +++ |
| 66 | CH₃S– | 2CH₃ | H | H | –N(piperidinyl)–CH₃ | – | 0 | +++ |
| 67 | CH₃S– | 2CH₃ | H | H | –NH–(CH₂)₇–CH₃ | – | ++ | ++++ |
| 68 | CH₃S– | 3Cl | 5CH₃ | H | –NH–(CH₂)₇–CH₃ | – | + | ++++ |
| 69 | CH₃S– | 2Cl | H | H | –N(piperidinyl)–CH₃ | – | + | +++ |
| 70 | CH₃S– | 2Cl | H | H | –NH–C(CH₃)₃ | – | ++ | + |
| 71 | CH₃S– | 2Cl | H | H | –NH–CH(CH₃)–CH₂CH₃ | – | ++ | + |
| 72 | CH₃SO₂– | 3CH₃ | H | H | –NH–CH(CH₃)₂ | 728 | + | + |
| 73 | C₂H₅S– | 3CH₃ | H | H | –NH–C(CH₃)₃ | 220 | ++ | ++++ |
| 74 | C₂H₅S– | 3CH₃ | H | H | –NH–CH(CH₃)₂ | 150 | ++ | +++ |
| 75 | C₂H₅S– | 3CH₃ | H | H | –N(piperidinyl) | 182 | 0 | ++++ |
| 76 | C₂H₅S– | 3CH₃ | H | H | –NH–CH(CH₃)–CH₂–CH₃ | – | + | +++ |
| 77 | C₂H₅S– | 3CH₃ | H | H | –NH–(cyclohexyl) | 91 | + | ++++ |
| 78 | C₂H₅S– | 3CH₃ | H | H | –N(morpholinyl) | – | 0 | +++ |

TABLE III-continued

| No. | $R_1$ | $R_2$ | $R_3$ | $R_4$ | $-N\begin{subarray}{c}R_5\\R_6\end{subarray}$ | $LD_{50}$ intraperitoneal, mouse, mg/kg | Auricle of guinea pig [1] | Peripherical vasodilatator activity [2] |
|---|---|---|---|---|---|---|---|---|
| 79 | $C_2H_5S-$ | $3CH_3$ | H | H | $-NH-\langle H \rangle$ | 91 | ++ | +++ |
| 80 | $C_2H_5S-$ | $3CH_3$ | H | H | $-NH-(CH_2)_3-CH_3$ | 110 | ++ | +++ |
| 81 | $C_2H_5S-$ | $3CH_3$ | H | H | $-NH-CH_2-CH_2-\langle\rangle$ | 75 | 0 | +++ |
| 82 | $C_2H_5S-$ | $3CH_3$ | H | H | $-NH-(CH_2)_2-CH_3$ | — | 0 | +++ |
| 83 | $C_2H_5S-$ | $3CH_3$ | H | H | $-NH-CH(CH_3)-CH_2-\langle\rangle$ | 110 | + | ++++ |
| 84 | $C_2H_5S-$ | $3CH_3$ | H | H | $-N\langle\rangle-CH_3$ | — | + | +++ |
| 85 | $isoC_3H_9S-$ | $3CH_3$ | H | H | $-N\langle\rangle-CH_3$ | 182 | ++ | ++++ |
| 86 | $isoC_3H_9S-$ | $3CH_3$ | H | H | $-N\langle\rangle$ | 110 | ++ | +++ |
| 87 | $isoC_3H_9S-$ | $3CH_3$ | H | H | $-NH-isoC_3H_7$ | — | + | +++ |
| 88 | $isoC_3H_9S-$ | $3CH_3$ | H | H | $-NH-(CH_2)_2-CH_3$ | — | + | ++++ |
| 89 | $nC_4H_9S-$ | $3CH_3$ | H | H | $-NHisoC_3H_7$ | — | + | +++ |
| 90 | $nC_4H_9S-$ | $3CH_3$ | H | H | $-NH-C(CH_3)_3$ | 91 | 0 | ++++ |
| 91 | $nC_4H_9S-$ | $3CH_3$ | H | H | $-NH-\langle H \rangle$ | 46 | + | ++++ |
| 92 | $nC_4H_9S-$ | $3CH_3$ | H | H | $-NH-\langle H \rangle$ | 182 | + | ++++ |
| 93 | $nC_4H_9S-$ | $3CH_3$ | H | H | $-N\langle\rangle$ | 182 | ++ | ++++ |
| 94 | $nC_4H_9S-$ | $3CH_3$ | H | H | $-N(CH_3)_2$ | 150 | 0 | ++ |
| 95 | $nC_4H_9S-$ | $3CH_3$ | H | H | $-N\langle\rangle_{CH_3}$ | 150 | ++ | ++++ |
| 96 | $nC_4H_9S-$ | $3CH_3$ | H | H | $-N\langle\rangle-CH_3$ | 182 | ++ | ++++ |
| 97 | $nC_4H_9S-$ | $3CH_3$ | H | H | $-NH-(CH_2)_3-CH_3$ | 110 | 0 | ++++ |
| 98 | $nC_4H_9S-$ | $3CH_3$ | H | H | $-N\langle\rangle$ | — | ++ | +++ |
| 99 | $nC_4H_9S-$ | $3CH_3$ | H | H | $-N\langle\rangle$ | — | + | +++ |
| 100 | $nC_4H_9S-$ | $3CH_3$ | H | H | $-NH-(CH_2)_3OCH_3$ | — | ++ | + |
| 101 | $nC_4H_9S-$ | $3CH_3$ | H | H | $-NH-CH_2CH=CH_2$ | — | ++ | ++ |
| 102 | $nC_5H_{11}S-$ | $3CH_3$ | H | H | $-NH-C(CH_3)_3$ | 91 | 0 | +++ |
| 103 | $nC_5H_{11}S-$ | $3CH_3$ | H | H | $-N\langle\rangle$ | 880 | ++ | ++ |
| 104 | $nC_5H_{11}S-$ | $3CH_3$ | H | H | $-NH-(CH_2)_3-CH_3$ | 75 | 0 | ++++ |
| 105 | $nC_5H_{11}S-$ | $3CH_3$ | H | H | $-N\langle\rangle-CH_3$ | — | + | ++++ |
| 106 | $nC_6H_{13}S-$ | $3CH_3$ | H | H | $-NH-CH-(CH_3)_2$ | — | 0 | ++++ |
| 107 | $nC_6H_{13}S-$ | $3CH_3$ | H | H | $-NH-C(CH_3)_3$ | 110 | 0 | ++++ |
| 108 | $nC_6H_{13}S-$ | $3CH_3$ | H | H | $-N\langle\rangle$ | 182 | + | ++++ |
| 109 | $nC_6H_{13}S-$ | $3CH_3$ | H | H | $-N\langle\rangle O$ | 600 | + | ++++ |

TABLE III-continued

| | COMPOUNDS | | | | $LD_{50}$ intraperitoneal, mouse, mg/kg | Auricle of guinea pig[1] | Peripherical vasodilatator activity[2] |
|---|---|---|---|---|---|---|---|
| No. | $R_1$ | $R_2$ | $R_3$ | $R_4$ $-N\begin{smallmatrix}R_5\\R_6\end{smallmatrix}$ | | | |
| 110 | $nC_6H_{13}S-$ | $3CH_3$ | H | H | $-N(CH_3)_2$ | — | 0 | +++ |
| 111 | $nC_6H_{13}S-$ | $3CH_3$ | H | H | $-NH(CH_2)_3CH_3$ | — | + | ++++ |
| 112 | $nC_6H_{13}S-$ | $3CH_3$ | H | H | $-NH-(CH_2)_2-CH_3$ | 364 | + | ++ |
| 113 | $nC_8H_{17}S-$ | $3CH_3$ | H | H | $-NH-CH-(CH_3)_2$ | — | ++ | +++ |
| 114 | $nC_8H_{17}S-$ | $3CH_3$ | H | H | $-NH-(CH_2)_3-CH_3$ | — | ++ | ++++ |
| 115 | $nC_8H_{17}S-$ | $3CH_3$ | H | H | $-N\bigcirc-CH_3$ (piperidine) | — | + | ++ |
| 116 | $nC_8H_{17}S-$ | $3CH_3$ | H | H | $-N\bigcirc$ (piperidine) | — | ++ | + |
| 117 | $nC_8H_{17}S-$ | $3CH_3$ | H | H | $-NH-CH(CH_3)-CH_2-CH_3$ | — | ++ | |
| 118 | $nC_{10}H_{21}S-$ | $3CH_3$ | H | H | $-NH-CH(CH_3)-CH_2-CH_3$ | — | + | ++ |
| 119 | $nC_{10}H_{21}S-$ | $3CH_3$ | H | H | $-NH-C(CH_3)_3$ | — | 0 | ++ |
| 120 | $nC_{10}H_{21}S-$ | $3CH_3$ | H | H | $-N\bigcirc$ | — | 0 | ++ |
| 121 | $nC_{10}H_{21}S-$ | $3CH_3$ | H | H | $-N\bigcirc-CH_3$ | — | 0 | ++ |
| 122 | $nC_{10}H_{21}S-$ | $3CH_3$ | H | H | $-NH-(CH_2)_7-CH_3$ | — | 0 | ++++ |
| 123 | $C_2H_5S-$ | $3CH_3$ | H | H | $-NH-(CH_2)_7-CH_3$ | — | 0 | ++++ |
| 124 | $isoC_3H_7S-$ | $3CH_3$ | H | H | $-N\bigcirc$ | 150 | ++ | ++++ |
| 125 | $isoC_3H_7S-$ | $3CH_3$ | H | H | $-NH-C(CH_3)_3$ | 150 | 0 | ++++ |
| 126 | $isoC_3H_7S-$ | $3CH_3$ | H | H | $-N\bigcirc O$ (morpholine) | 440 | 0 | ++ |
| 127 | $isoC_3H_7S-$ | $3CH_3$ | H | H | $-NH-CH(CH_3)_2$ | 182 | ++ | ++++ |
| 128 | $isoC_3H_7S-$ | $3CH_3$ | H | H | $-NH-CH(CH_3)-CH_2-CH_3$ | — | + | ++++ |
| 129 | $isoC_3H_7S-$ | $3CH_3$ | H | H | $-NH-(CH_2)_3-CH_3$ | 46 | ++ | ++++ |
| 130 | $isoC_3H_7S-$ | $3CH_3$ | H | H | $-NH-\bigcirc(H)$ (cyclohexyl) | 75 | 0 | ++++ |
| 131 | $isoC_3H_7S-$ | $3CH_3$ | H | H | $-NH-(CH_2)_7-CH_3$ | 86 | 0 | ++++ |
| 132 | $isoC_3H_7S-$ | $3CH_3$ | H | H | $-NH-(CH_2)_2-\bigcirc$ (phenyl) | 110 | + | ++++ |
| 133 | $isoC_3H_7S-$ | $3CH_3$ | H | H | $-N\bigcirc-CH_3$ | 110 | + | +++ |
| 134 | $isoC_3H_7S-$ | $2CH_3$ | H | H | $-NH-CH(CH_3)_2$ | — | + | +++ |
| 135 | $isoC_3H_7S-$ | $2CH_3$ | H | H | $-NH-C(CH_3)_3$ | — | + | +++ |
| 136 | $nC_3H_7S-$ | $3CH_3$ | H | H | $-NH-CH(CH_3)_2$ | — | ++ | ++ |
| 137 | $CH_3S-$ | $3Cl$ | H | H | $-NH-CH(CH_3)-CHOH-\bigcirc$ | — | + | ++ |
| 138 | $CH_3S-$ | $3F$ | H | H | $-NH-C(CH_3)_3$ | — | + | ++ |
| 139 | $CH_3S-$ | $3CH_3$ | H | H | $-N(nC_3H_7)_2$ | 0 | ++ | |
| 140 | $CH_3S-$ | $3F$ | H | H | $-NH-(CH_2)_7-CH_3$ | — | + | ++++ |
| 141 | $CH_3S-$ | H | H | H | $-NH-(CH_2)_7-CH_3$ | — | + | ++++ |
| 142 | $CH_3S-$ | $3F$ | H | H | $-NH-CH(CH_3)-CH_2-CH_3$ | — | + | ++ |
| 143 | $CH_3S-$ | $3F$ | H | H | $-NH-(CH_2)_3-CH_3$ | — | 0 | ++ |
| 144 | $CH_3S-$ | $3CH_3$ | H | H | $-N(cycloC_6H_{11})_2$ | — | + | ++ |
| 145 | $CH_3S-$ | $3COOCH_3$ | H | H | $-N\bigcirc$ | — | + | ++ |

TABLE III-continued

| No. | R₁ | R₂ | R₃ | R₄ | -N(R₅)(R₆) | LD₅₀ intraperitoneal, mouse, mg/kg | Auricle of guinea pig[1] | Peripherical vasodilatator activity[2] |
|---|---|---|---|---|---|---|---|---|
| 146 | $CH_3S-$ | $3CH_3$ | H | H | $-NH-CH(CH_3)-CH_2-CH_2-C_6H_5$ | — | + | ++ |
| 147 | $CH_3S-$ | $3CH_3$ | H | H | -N(piperidine)-OH | — | + | ++ |
| 148 | $CH_3S-$ | $3CH_3$ | H | H | -N(piperidine with $C_2H_5$) | — | + | +++ |
| 149 | $CH_3S-$ | $3CH_3O$ | H | H | -N(piperidine) | — | + | ++ |
| 150 | $CH_3S-$ | $3CH_3$ | H | H | -N(piperazine)-pyridyl, $CH_3$ | — | — | +++ |
| 151 | $CH_3S-$ | $3CH_3$ | H | H | -N(piperazine)-phenyl-$CH_3$ | — | + | ++ |
| 152 | $CH_3S-$ | $3CH_3$ | H | H | $-NH-CH(CH_3)-CH_2-CH(CH_3)_2$ | — | + | +++ |
| 153 | $CH_3S-$ | $3CH_3$ | H | H | $NH-CH(CH_3)-CH(CH_3)_2$ | — | + | ++++ |
| 154 | $CH_3S-$ | 2Cl | H | H | $-NH-CH(CH_3)_2$ | — | + | ++ |
| 155 | $CH_3SO_2$ | $3CH_3$ | H | H | -N(piperidine) | — | + | ++ |
| 156 | $isoC_3H_7S-$ | $3CH_3$ | H | $C_2H_5$ | $-NH-(CH_2)_7-CH_3$ | — | + | ++++ |
| 157 | $isoC_3H_7S-$ | $3CH_3$ | H | H | $-NH-(CH_2)_6-CH_3$ | — | + | ++++ |
| 157 | $isoC_3H_7S-$ | $3CH_3$ | H | $CH_3$ | $-NH-(CH_2)_7-CH_3$ | — | + | ++++ |
| 158 | $nC_3H_7S-$ | $3CH_3$ | H | H | $-NH-(CH_2)_5-CH_3$ | — | + | +++ |
| 159 | $nC_3H_7S-$ | $3CH_3$ | H | H | $-NH-(CH_2)_7-CH_3$ | — | + | ++++ |
| 160 | $nC_3H_7S-$ | $3CH_3$ | H | H | $-NH-CH(CH_3)-CH_2-CH_3$ | — | + | +++ |
| 161 | $nC_4H_9S-$ | $3CH_3$ | H | H | $-NH-CH(CH_3)-CHOH-$ | — | 0 | ++++ |
| | Propranolol | | | | | 110 | ++ | +++ |
| | Papaverine | | | | | 300 | 0 | +++ |

[1](β-lytic activity) O = inactive; + = low activity; ++ = high activity (dose = 1 × 10⁻⁸ g/ml)
[2]O = inactive; + = low activity; ++ = mean activity; +++ = activity equal to that of papaverine; ++++ = activity higher than that of papaverine (dose = 30 γ/kg intra-arterial)

TABLE IV

| No. | R₁ | R₂ | R₃ | R₄ | -N(R₅)(R₆) | Local anaesthesic activity[3] | Anti-arrhythmic activity[4] |
|---|---|---|---|---|---|---|---|
| 1 | $CH_3S-$ | $3CH_3$ | H | H | $-NH-CH(CH_3)_2$ | 4.5(3.5-5.9) | 12/20 |
| 2 | $CH_3S-$ | 3Cl | H | H | $-NH-C(CH_3)_3$ | — | 1/10 |
| 3 | $CH_3S-$ | 3Cl | H | $CH_3$ | $-NH-C(CH_3)_3$ | >5 | 1/10 |
| 4 | $CH_3S-$ | $3CH_3$ | H | $CH_3$ | $-NH-(CH_2)_3CH_3$ | >5 | — |
| 5 | $CH_3S-$ | 3Cl | H | H | $-NH-CH(CH_3)-CH_2-CH_3$ | >5 | — |
| 6 | $CH_3S-$ | 3Cl | H | H | $-NH-CH(CH_3)_2$ | >5 | 11/20 |
| 7 | $CH_3S-$ | $3CH_3$ | H | H | $-NH-C(CH_3)_3$ | 4(2.2-7.6) | — |
| 8 | $CH_3S-$ | $3CH_3$ | H | H | -N(piperidine) | 1.6(1-2.4) | 2/10 |
| 9 | $CH_3S-$ | 3Cl | H | H | $-NH-(CH_2)_2-CH_3$ | >5 | — |
| 10 | $CH_3S-$ | 3Cl | H | H | $-NH-(CH_2)_3-CH_3$ | >5 | — |
| 11 | $CH_3S-$ | 3Cl | H | $C_2H_5$ | $-NH-CH(CH_3)_2$ | >5 | — |
| 12 | $CH_3S-$ | 3Cl | H | $C_2H_5$ | $-NH-CH(CH_3)-CH_2CH_3$ | >5 | 0/10 |

TABLE IV-continued

| No. | R₁ | R₂ | R₃ | R₄ | -N(R₅)(R₆) | Local anaesthesic activity[a] | Anti-arrhythmic activity[d] |
|---|---|---|---|---|---|---|---|
| 13 | CH₃S— | 3Cl | H | C₂H₅ | —NH—C(CH₃)₃ | >5 | — |
| 14 | CH₃S— | 3CH₃ | H | CH₃ | -N◯-CH₃ | 2.9(2-4.2) | 2/10 |
| 15 | CH₃S— | 3CH₃ | H | CH₃ | —N(CH₃)₂ | >5 | 1/10 |
| 16 | CH₃S— | 3Cl | H | H | -N◯O | — | 2/10 |
| 17 | CH₃S— | 3Cl | H | H | -N◯ | — | 2/10 |
| 18 | CH₃S— | 2CH₃ | H | CH₃ | -N◯ | — | 1/10 |
| 19 | CH₃S— | 3Cl | H | C₂H₅ | —N(CH₃)₂ | >5 | — |
| 20 | CH₃S— | 3Cl | H | C₂H₅ | -N◯O | >5 | — |
| 21 | CH₃S— | 3CH₃ | H | H | -NH-◯(H) | 3.4(2.1-5.6) | — |
| 22 | CH₃S— | 3CH₃ | H | H | —NH—(CH₂)₃CH₃ | >5 | — |
| 23 | CH₃S— | 3CH₃ | H | H | —NH—CH(CH₃)—CH₂—CH₃ | ∓5 | 4/10 |
| 24 | CH₃S— | 3CH₃ | H | H | -NH-◯(H) | >5 | 4/10 |
| 25 | CH₃S— | 3CH₃ | H | C₂H₅ | —NH—CH(CH₃)₂ | >5 | 2/10 |
| 26 | CH₃S— | 3CH₃ | H | C₂H₅ | —NH—C(CH₃)₃ | >5 | — |
| 27 | CH₃S— | 3CH₃ | H | H | -N◯-CH₃ | >5 | 2/10 |
| 28 | CH₃S— | 3C₂H₅ | H | H | —NH—(CH₂)₇—CH₃ | >5 | — |
| 29 | CH₃S— | 3C₂H₅ | H | H | -N◯ | >5 | 4/10 |
| 30 | CH₃S— | 3C₂H₅ | H | H | —NH—CH(CH₃)₂ | — | 13/20 |
| 31 | CH₃S— | 3C₂H₅ | H | H | -N◯-CH₃ | >5 | — |
| 32 | CH₃S— | 3CH₃ | H | H | —NH—CH(CH₃)—CH₂—◯—CH₃ | — | — |
| 33 | CH₃S— | 3CH₃O | H | H | —NH—C(CH₃)₃ | — | 2/10 |
| 34 | CH₃S— | 3CH₃ | H | H | -N◯-CH₃ | ∓5 | — |
| 35 | CH₃S— | 3C₂H₅ | H | H | —NH—C(CH₃)₃ | >5 | 5/10 |
| 36 | CH₃S— | 3C₂H₅ | H | H | —NH—CH(CH₃)—CH₂—CH₃ | >5 | 6/10 |
| 37 | CH₃S— | 3Cl | H | H | -N◯-CH₃ | >5 | 1/10 |
| 38 | CH₃S— | 3Cl | H | H | —NH—(CH₂)₃OCH₃ | >5 | — |
| 39 | CH₃S— | 3F | H | H | —NH—CH(CH₃)₂ | >5 | 2/10 |
| 40 | CH₃S— | 3Cl | H | nC₃H₇ | —NH—CH(CH₃)—CH₂—CH₃ | ±5 | — |
| 41 | CH₃S— | 3COOCH₃ | H | H | -N◯ | >5 | — |
| 42 | CH₃S— | 2CH₃ | H | H | —NH—C(CH₃)₃ | ±7 | — |
| 43 | CH₃S— | 3Cl | 5CH₃ | H | —NH—CH(CH₃)₂ | 4.1(2.5-6.9) | — |
| 44 | CH₃S— | 2Cl | H | H | -N◯-CH₃ | 4.15(2-8.6) | 1/10 |
| 45 | CH₃S— | 2Cl | H | H | -N◯ | >5 | — |
| 46 | CH₃S— | 2Cl | H | H | —NH—C(CH₃)₃ | — | 3/10 |
| 47 | CH₃SO₂ | 3CH₃ | H | H | —NH—CH(CH₃)₂ | >5 | 13/20 |
| 48 | C₂H₅S— | 3CH₃ | H | H | —NH—CH(CH₃)₂ | ±5 | — |
| 49 | C₂H₅S— | 3CH₃ | H | H | —NH—CH(CH₃)₂ | >10 | 2/10 |

3,954,871

TABLE IV-continued

| No. | R₁ | R₂ | R₃ | R₄ | $-N\binom{R_5}{R_6}$ | Local anaesthesic activity[3] | Anti-arrhythmic activity[4] |
|---|---|---|---|---|---|---|---|
| 50 | C₂H₅S— | 3CH₃ | H | H | -N⟨piperidine⟩ | — | — |
| 51 | C₂H₅S— | 3CH₃ | H | H | -NH-⟨cyclohexyl⟩ | >5 | — |
| 52 | C₂H₅S— | 3CH₃ | H | H | -NH-⟨cyclopentyl⟩ | >5 | 3/10 |
| 53 | C₂H₅S— | 3CH₃ | H | H | —NH—(CH₂)₃CH₃ | >5 | — |
| 54 | C₂H₅S— | 3CH₃ | H | H | —NH—(CH₂)₂—CH₃ | >5 | — |
| 55 | C₂H₅S— | 3CH₃ | H | H | -NH-CH(CH₃)-CH₂-⟨C₆H₅⟩ | — | — |
| 56 | C₂H₅S— | 3CH₃ | H | H | -N⟨piperidine⟩-CH₃ | >5 | — |
| 57 | isoC₃H₇S— | 3CH₃ | H | H | -N⟨piperidine⟩ | >5 | 3/10 |
| 58 | isoC₃H₇S— | 3CH₃ | H | H | —NH-isoC₃H₇ | >5 | — |
| 59 | isoC₃H₇S— | 3CH₃ | H | H | —NH—(CH₂)₇—CH₃ | — | 3/10 |
| 60 | nC₃H₇S— | 3CH₃ | H | H | —NHisoC₃H₇ | — | 1/10 |
| 61 | nC₄H₉S— | 3CH₃ | H | H | -N⟨piperidine⟩ | 1.9(1.4–2.7) | 5/10 |
| 62 | nC₄H₉S— | 3CH₃ | H | H | -N⟨piperidine⟩-CH₃ | >5 | — |
| 63 | nC₄H₉S— | 3CH₃ | H | H | -N⟨piperidine⟩-CH₃ | 4.1(3–5.6) | 2/10 |
| 64 | nC₄H₉S— | 3CH₃ | H | H | —NH—(CH₂)₃OCH₃ | — | 4/10 |
| 65 | nC₄H₉S— | 3CH₃ | H | H | —NH—CH₂—CH=CH₂ | — | 1/10 |
| 66 | nC₄H₉S— | 3CH₃ | H | H | -NH-CH(CH₃)-CHOH-⟨C₆H₅⟩ | — | 2/10 |
| 67 | nC₅H₁₁S— | 3CH₃ | H | H | -N⟨piperidine⟩ | >5 | — |
| 68 | nC₆H₁₃S— | 3CH₃ | H | H | —NH—CH—(CH₃)₂ | >5 | 1/10 |
| 69 | nC₈H₁₇S— | 3CH₃ | H | H | —NH—CH—(CH₃)₂ | >5 | — |
| 70 | nC₈H₁₇S— | 3CH₃ | H | H | -N⟨piperidine⟩ | >5 | 3/10 |
| 71 | nC₈H₁₇S— | 3CH₃ | H | H | —NH—CH(CH₃)—CH₂—CH₃ | — | 3/10 |
| 72 | nC₁₀H₂₁S— | 3-CH₃ | H | H | -N⟨piperidine⟩ | >5 | — |
| 73 | nC₁₀H₂₁S— | 3-CH₃ | H | H | —NH—CH—(CH₃)₂ | >5 | — |
| 74 | isoC₃H₇S— | 3CH₃ | H | H | -N⟨piperidine⟩ | 3.5(2.5–4.9) | — |
| 75 | isoC₃H₇S— | 3CH₃ | H | H | —NH—C(CH₃)₃ | >5 | 4/10 |
| 76 | isoC₃H₇S— | 3CH₃ | H | H | —NH—CH(CH₃)₂ | 2.35(1.7–3.2) | 10/20 |
| 77 | isoC₃H₇S— | 3CH₃ | H | H | —NH—(CH₂)₃—CH₃ | >5 | 3/10 |
| 78 | isoC₃H₇S— | 3CH₃ | H | H | —NH-(CH₂)₇—CH₃ | — | 2/10 |
| 79 | isoC₃H₇S— | 2CH₃ | H | H | —NH—CH(CH₃)₂ | >5 | 1/10 |
| Propranolol | | | | | | 1.4(0.9–2.2) | 20/20 |
| Papaverine | | | | | | — | — |
| Procaine | | | | | | 1.8(0.79–4.15) | — |
| Quinidine | | | | | | — | 4/20 |

[3]ED₅₀(mg/kg)
[4]Number of mice protected in relation with the number of tested mice (dose = 100 mg/kg per os; recording 30 min. after administration)

TABLE V

| | | | Protection against anoxia (isolated auricles of guinea pigs) |
|---|---|---|---|
| $R_3 = R_4 = H$ | | | |
| $R_1$ | $R_2$ | $N\langle{}^{R_5}_{R_6}$ | Activity[1] |
| $CH_3S-$ | $3CH_3$ | $-NHisoC_3H_7$ | ++ |
| $CH_3S-$ | $3Cl$ | $-NHisoC_3H_7$ | ++ |
| $CH_3S-$ | $3CH_3$ | $-N\bigcirc$ (piperidine) | + |
| $CH_3S-$ | $3CH_3$ | $-NH-C(CH_3)_3$ | + |
| $CH_3S-$ | $3CH_3$ | $-NH-\bigcirc H$ (cyclohexyl) | ++ |
| $CH_3S-$ | $3C_2H_5$ | $-NHisoC_3H_7$ | ++ |
| Propranolol | | | 0 |
| Papaverine | | | 0 |

[1] + means an average protecting activity is present
++ means a high protecting activity is present (dose: 1.10 - 6 g/ml of bath)

The products according to the invention can be presented in various forms, following examples being not limitative:

Injectable solution

— 5 mg of 1-(3-methyl-4-methylthiophenyl)-2-isopropylaminoethanol hydrochloride
— 41.7 mg of sodium chloride
— 5 ml of water
— sterilisation at 120°C.

Tablets

— 10 mg of 1-(3-methyl-4-methylthiophenyl)-2-isopropylaminoethanol hydrochloride
— 70 mg of lactose
— 1 mg of stearic acid
— 2 mg of gelatin
— 15 mg of starch The daily doses of the derivatives of the invention for humans, orally administrated, are in the range of 4 to 100 mg, while they are in the range of 5 to 20 mg by injection.

We claim:
1. Amino-alcohols having the general formula:

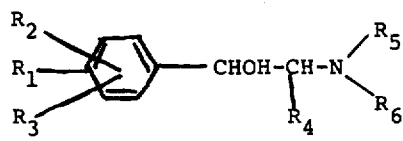

wherein: $R_1$ represents a RS or $RSO_2$ group in which R is a linear or branched alkyl ($C_1$-$C_{10}$) radical; $R_2$ and $R_3$, which may be identical or different, represent a chlorine or fluorine atom or an alkyl ($C_1$-$C_2$) radical; $R_4$ represents a hydrogen atom or a linear or branched alkyl ($C_1$-$C_3$) radical; $R_5$ and $R_6$ which may be identical or different, represent a hydrogen atom, a linear or branched alkyl ($C_1$-$C_{11}$) radical, a cycloalkyl ($C_5$-$C_6$) radical; $R_2$ and $R_3$ can also be both hydrogen except if simultaneously R is an alkyl radical ($C_1$-$C_3$) in the groups RS or $RSO_2$, $R_4$ and $R_5$ are hydrogen atoms and $R_6$ is an isopropyl or t butyl radical; one of $R_2$ and $R_3$ can also be a hydrogen atom, the other one being a chlorine or fluorine atom or an alkyl ($C_1$-$C_2$) radical; as well as hydrochlorides, hydrobromides, phosphates, sulfates, oxalates, lactates and gluconates of said amino-alcohols.

2. 1-(3-methyl-4-methylthiophenyl)-2-isopropylaminoethanol.

3. 1-(3-methyl-4-isopropylthiophenyl)-2-n.octylaminoethanol.

4. 1-(3-methyl-4-methylthiophenyl)-2-n.octylaminoethanol.

5. 1-(3-methy;-4-methylthiophenyl)-2-n-octylaminoethanol hydrochloride.

6. 1-(3-chloro-4-methylthiophenyl)-2-sec-butylaminopentanol hydrochloride.

7. 1-(3-methyl-4-isopropylthiophenyl)-2-n-octylaminopropanol hydrochloride.

8. 1-(3-methyl-4-methylthiophenyl)-2-isopropylaminoethanol hydrochloride.

9. 1-(3-methyl-4-isopropylthiophenyl)-2-n-octylaminoethanol hydrochloride.

\* \* \* \* \*